(12) United States Patent
Rodriguez

(10) Patent No.: US 9,744,419 B1
(45) Date of Patent: *Aug. 29, 2017

(54) VISION TRAINING SYSTEM AND METHOD OF USE

(71) Applicant: Dacks Rodriguez, Melbourne, FL (US)

(72) Inventor: Dacks Rodriguez, Melbourne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/256,021

(22) Filed: Sep. 2, 2016

Related U.S. Application Data

(63) Continuation-in-part of application No. 14/752,328, filed on Jun. 26, 2015, now Pat. No. 9,457,253.

(51) Int. Cl.
*A63B 69/36* (2006.01)
*A63B 69/00* (2006.01)

(52) U.S. Cl.
CPC ...... *A63B 69/0002* (2013.01); *A63B 69/3608* (2013.01); *A63B 2069/0008* (2013.01)

(58) Field of Classification Search
USPC ........ 473/210, 268, 422, 450, 451, 458, 464
See application file for complete search history.

(56) References Cited

U.S. PATENT DOCUMENTS

| | | | |
|---|---|---|---|
| 3,524,650 A * | 8/1970 | Brandell | A63B 69/36 359/804 |
| 3,577,566 A | 5/1971 | Kislin | |
| 3,868,108 A | 2/1975 | Kirchner | |
| 4,303,241 A | 12/1981 | Burroughs | |
| 4,392,650 A | 7/1983 | Hilton | |
| 4,605,226 A | 8/1986 | Morrissey | |
| 4,741,611 A | 5/1988 | Burns | |
| 4,953,967 A | 9/1990 | Somerville | |
| 4,989,274 A | 2/1991 | Patelski, III | |
| 5,076,681 A | 12/1991 | Lhospice | |
| 5,162,823 A | 11/1992 | Goldstein | |
| 5,521,653 A | 5/1996 | Anderson | |

(Continued)

OTHER PUBLICATIONS

GS Pitch-IQ trains baseball hitters by using the science of occlusion, retrieved from http://www.gamesensesports.com/ on Jan. 24, 2017, 10 pages.

(Continued)

*Primary Examiner* — Nini Legesse
(74) *Attorney, Agent, or Firm* — Brian S. Steinberger; Law Offices of Brian S. Steinberger, PA

(57) ABSTRACT

Devices, systems, and methods for training baseball and softball batters, to identify types of pitched balls (fast ball, curve ball, slider and changeup) and locations (strike or non-strike zone) of pitched balls in order to increase hitting accuracy A motion sensor can be triggered by the leading foot of a pitcher. The motion sensor can use cone or fan shaped sensor to detect the passage of a pitched ball from the pitcher. When the motion sensor is triggered, a signal can be sent to a black out lens that blocks the vision of a hitter being trained to identify the types and locations of the pitched balls. The training includes changing the lens from transparent to opaque at selected distances between the hitter and the pitcher. Batters can be trained to keep their eyes on the pitched balls until the ball reaches the batter. Golfers can be trained to not have to look up when their club hits the ball, where the black out lens are go opaque when the golf swing passes into the motion sensor.

20 Claims, 18 Drawing Sheets

(56) References Cited

U.S. PATENT DOCUMENTS

| | | |
|---|---|---|
| 5,661,534 A | 8/1997 | Gill |
| 6,513,928 B1 | 2/2003 | Moore |
| 6,983,741 B2 | 1/2006 | Donald |
| 7,048,371 B1 | 5/2006 | Moore |
| 7,328,997 B2 | 2/2008 | Russomagno et al. |
| 7,534,178 B2 | 5/2009 | Nicely |
| D608,815 S | 1/2010 | Markovitch |
| 7,758,184 B2 | 7/2010 | Hoeffner |
| 7,828,434 B2 | 11/2010 | Coulter et al. |
| 8,062,037 B1 | 11/2011 | Chapa, Jr. et al. |
| 8,091,150 B2 | 1/2012 | Bengochea |
| 8,209,770 B2 | 7/2012 | Page et al. |
| 8,296,869 B2 | 10/2012 | Kellogg |
| 8,342,685 B2 | 1/2013 | Yoo et al. |
| 8,387,169 B2 | 3/2013 | Shockman |
| 8,568,256 B1 | 10/2013 | Richardson |
| 8,595,949 B2 | 12/2013 | Reichow et al. |
| 8,696,126 B2 | 4/2014 | Too et al. |
| 8,714,740 B2 | 5/2014 | Reichow et al. |
| 8,747,260 B1 | 6/2014 | Glynn |
| 8,908,922 B2 | 12/2014 | Marty et al. |
| 8,948,457 B2 | 2/2015 | Marty et al. |
| 8,963,829 B2 | 2/2015 | Lee et al. |
| 9,314,376 B1 | 4/2016 | Sherer |
| 9,457,253 B1 * | 10/2016 | Rodriguez ......... A63B 69/0002 |
| 2006/0178236 A1 | 8/2006 | Mosbey |
| 2007/0005540 A1 | 1/2007 | Fadde |
| 2010/0255449 A1 | 10/2010 | Fadde |
| 2013/0095961 A1 * | 4/2013 | Marty ................ A63B 24/0003 473/450 |
| 2013/0330693 A1 | 12/2013 | Sada et al. |
| 2015/0273304 A1 | 10/2015 | Glynn |
| 2016/0074737 A1 | 3/2016 | Fadde |
| 2016/0129329 A1 | 5/2016 | Fadde |

OTHER PUBLICATIONS

Pavlovich, Jr., Lou, New Baseball Inventions Are Simply Amazing, retrieved from http://baseballnews.com/new-baseball-inventions-simply-amazing/ on Jan. 24, 2017, 14 pages.

GS gameSense Sports, The Leaders in Athlete Decision-Making, Frequently-Asked Questions, retrieved from http://www.gamesensesports.com/faq#vidoes-cut-off on Jan. 24, 2017, 5 pages.

Fadde, Peter J., Interactive Video Training of Perceptual Decision-Making in the Sport of Baseball, Tech., Inst., Cognition and Learning, 2006, vol. 4, 20 pages.

Visual Occlusion Glasses—2nd Generation, file:///C:/Users/Recpt/AppData/Local/Microsoft/Windows/Temporary%20Internet%20File . . . 2 pages.

* cited by examiner

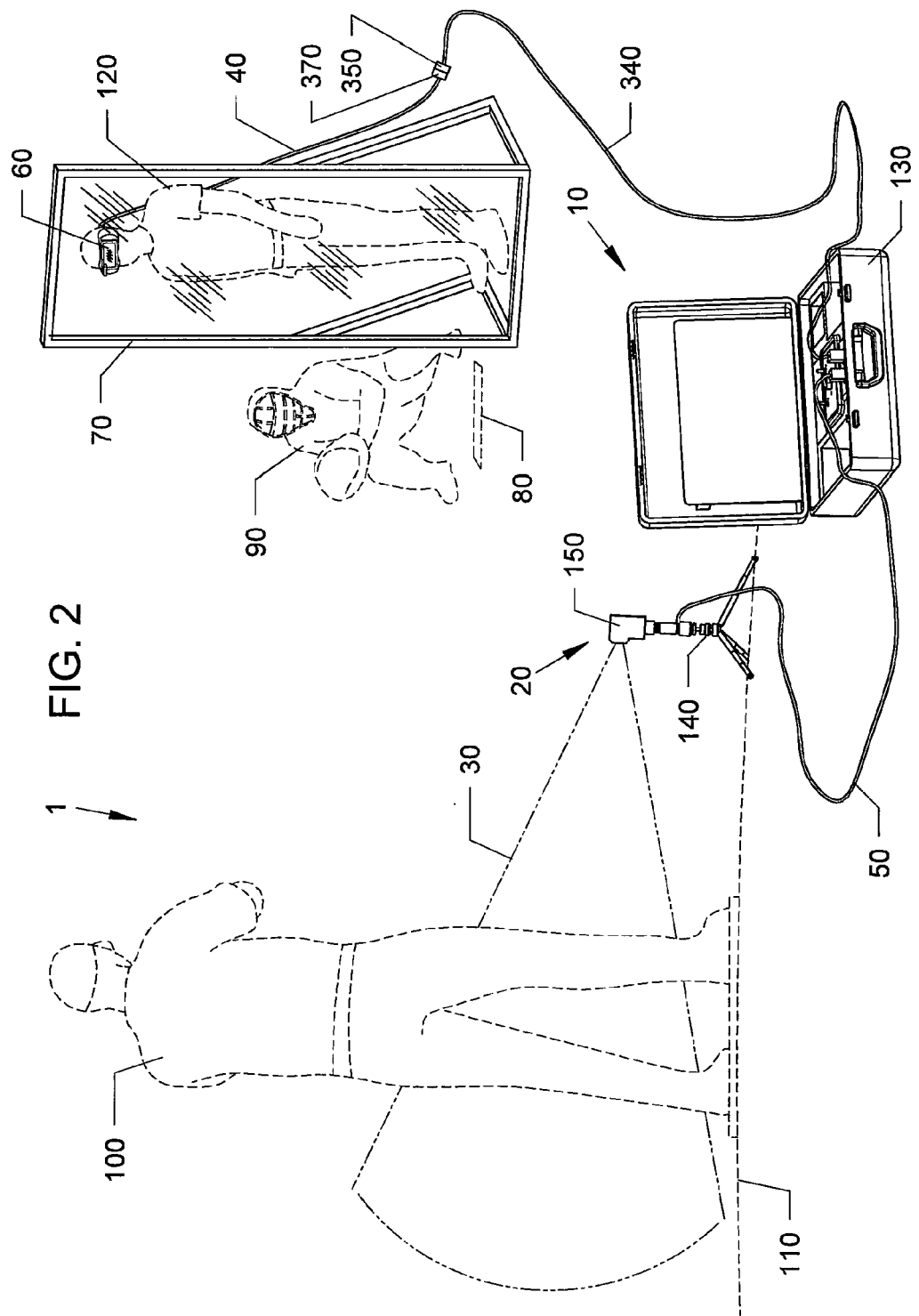

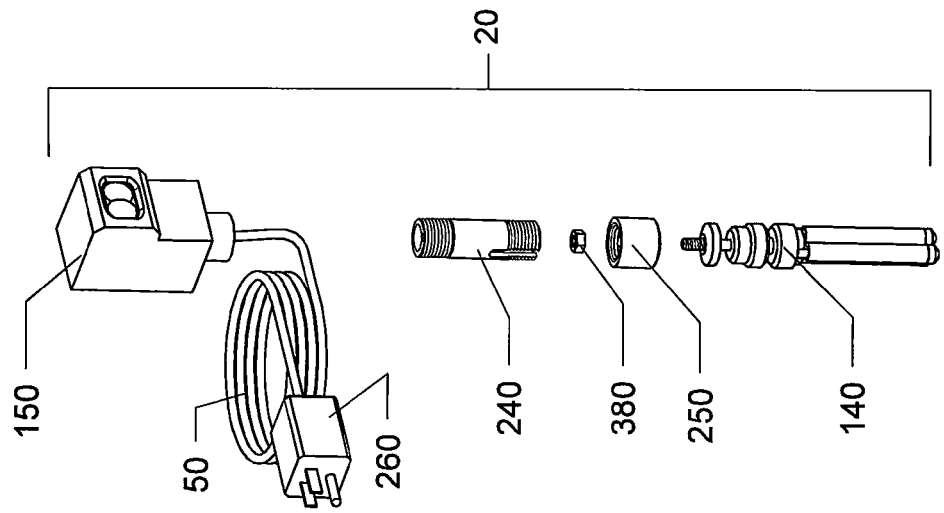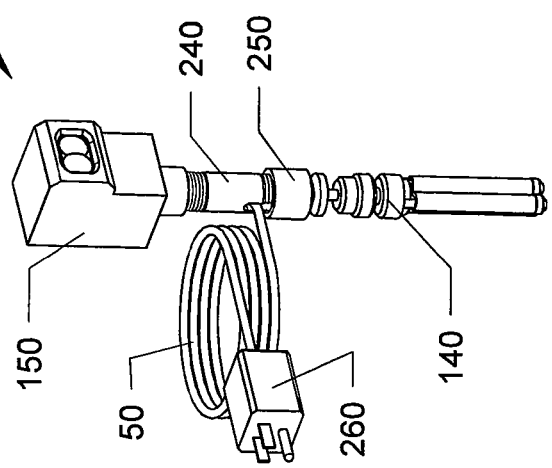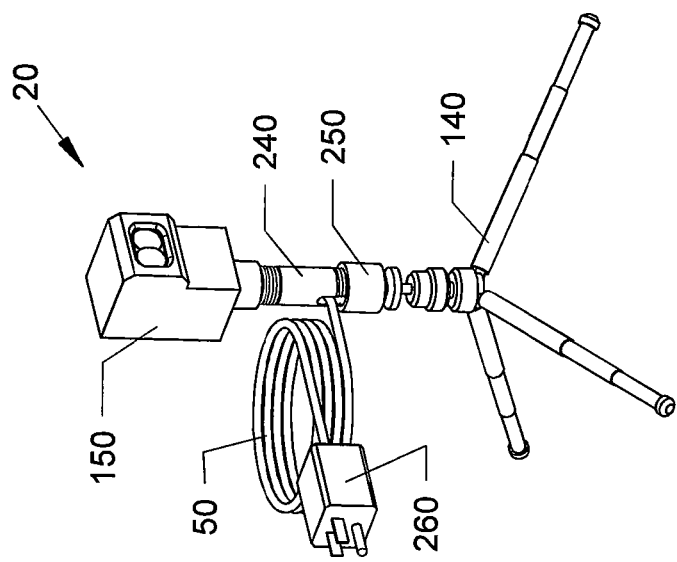

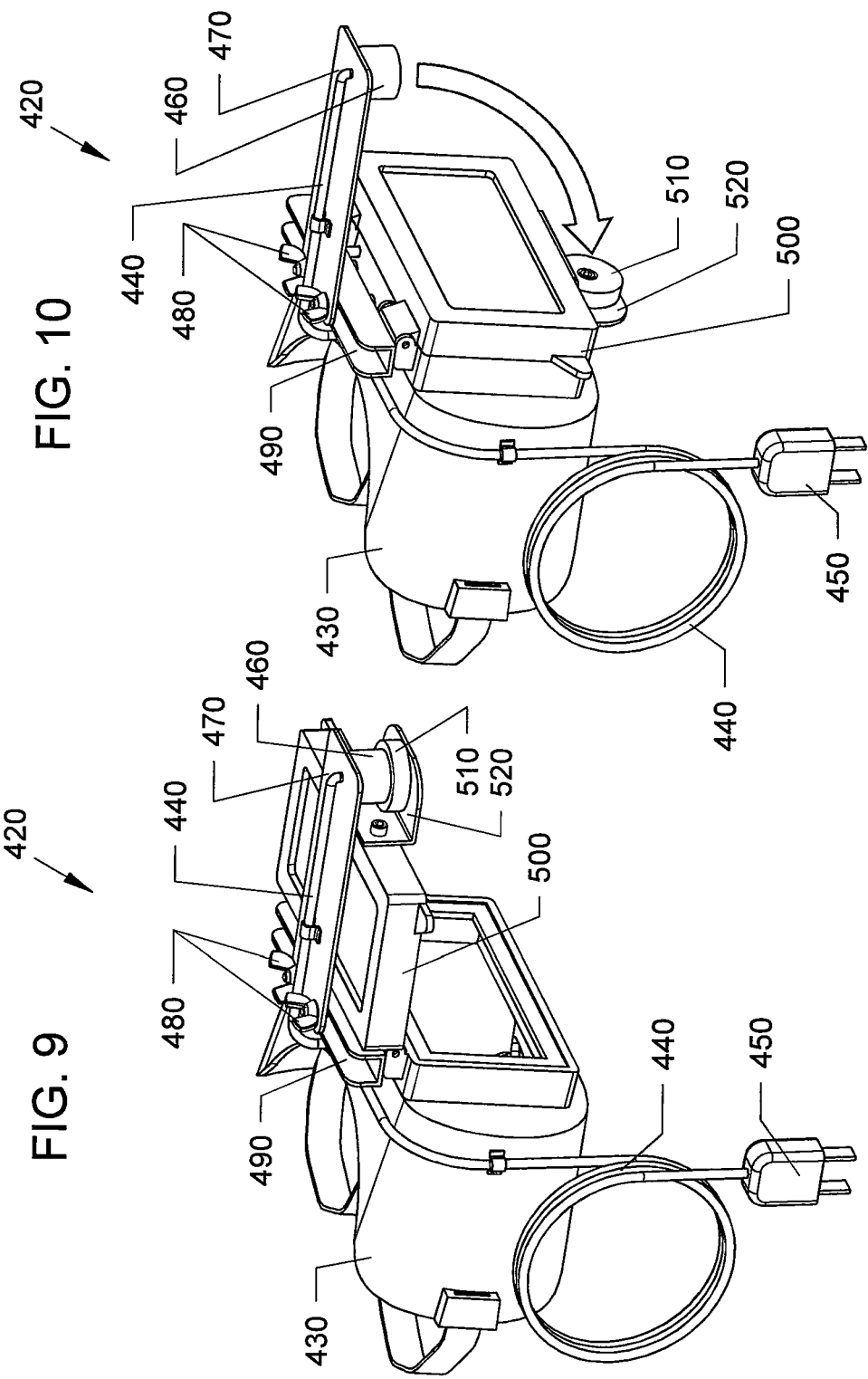

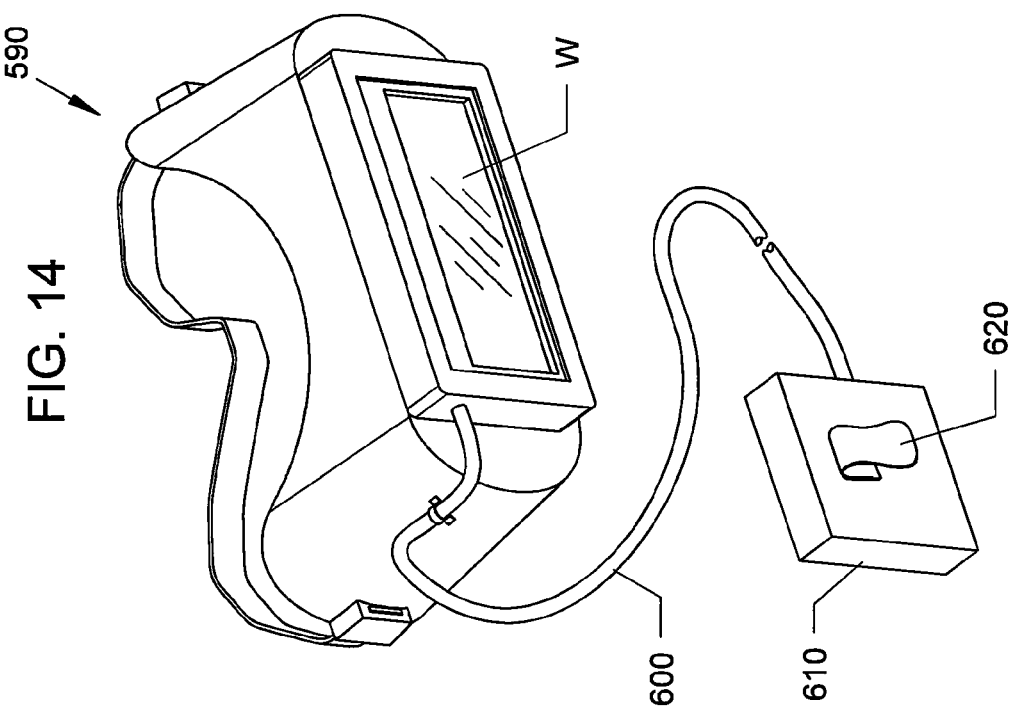
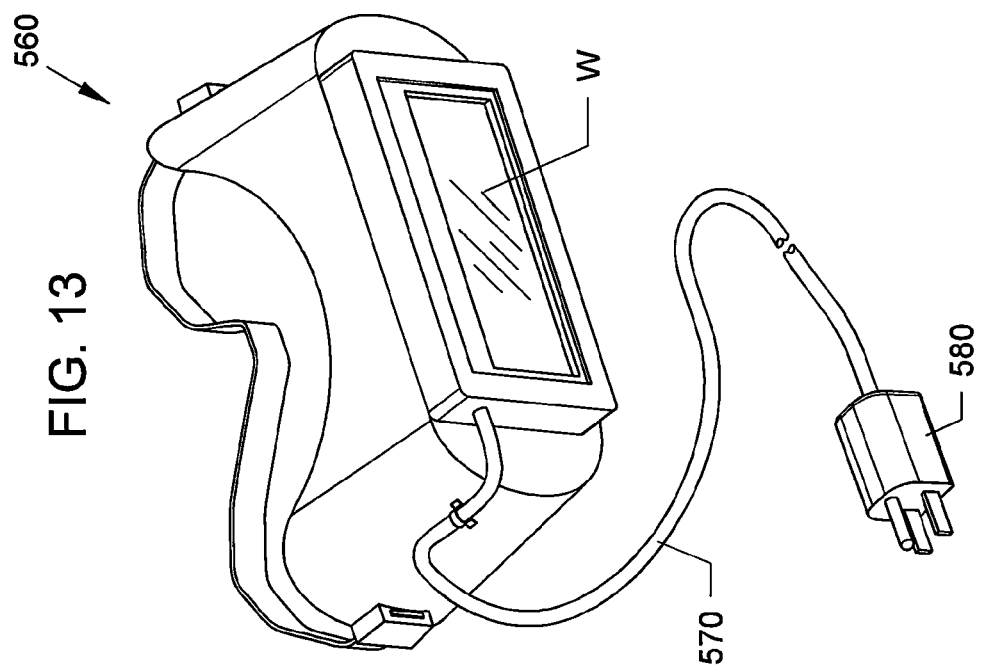

FIG. 17　　　　PITCH CHART
PLAYER NAME _____   DATE _____
PITCH 1 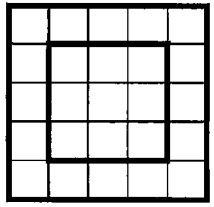　　PITCH 2 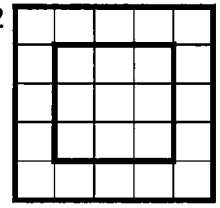
PITCH 3 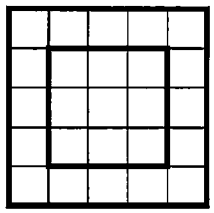　　PITCH 4 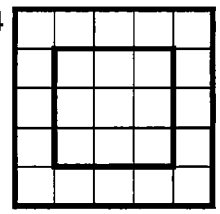
PITCH 5 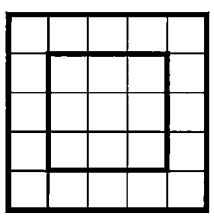　　PITCH 6 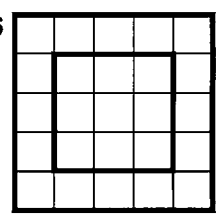
PITCH 7 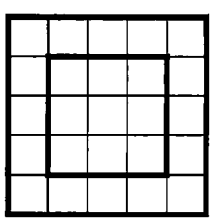　　PITCH 8 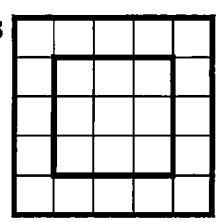
PITCH 9 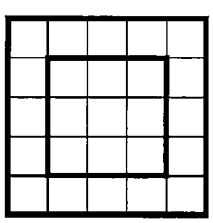　　PITCH 10 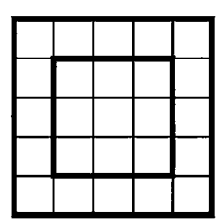
PITCH: ____ OF 10
LOCATION: ____ OF 10
DISTANCE: ____

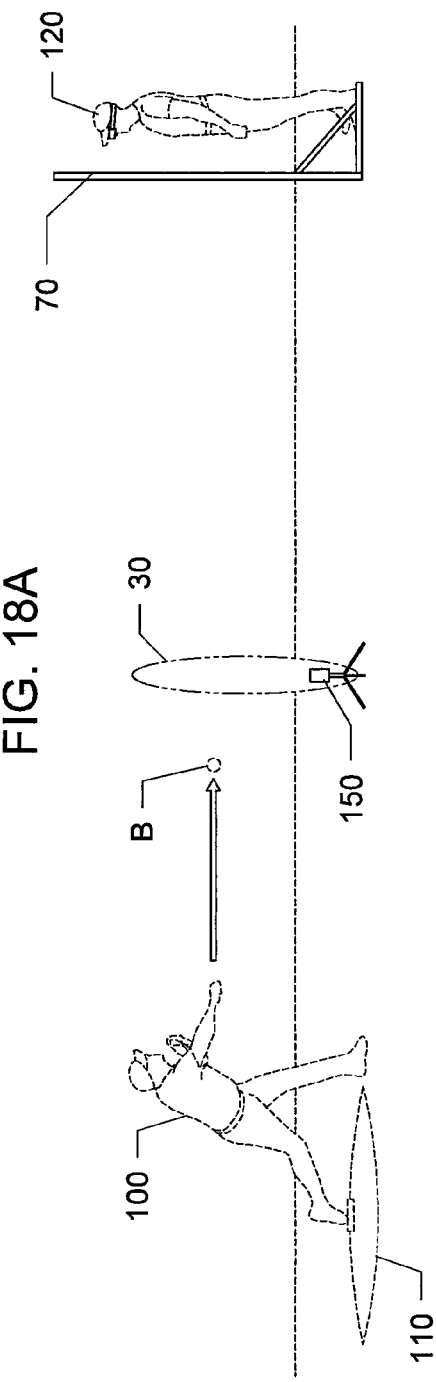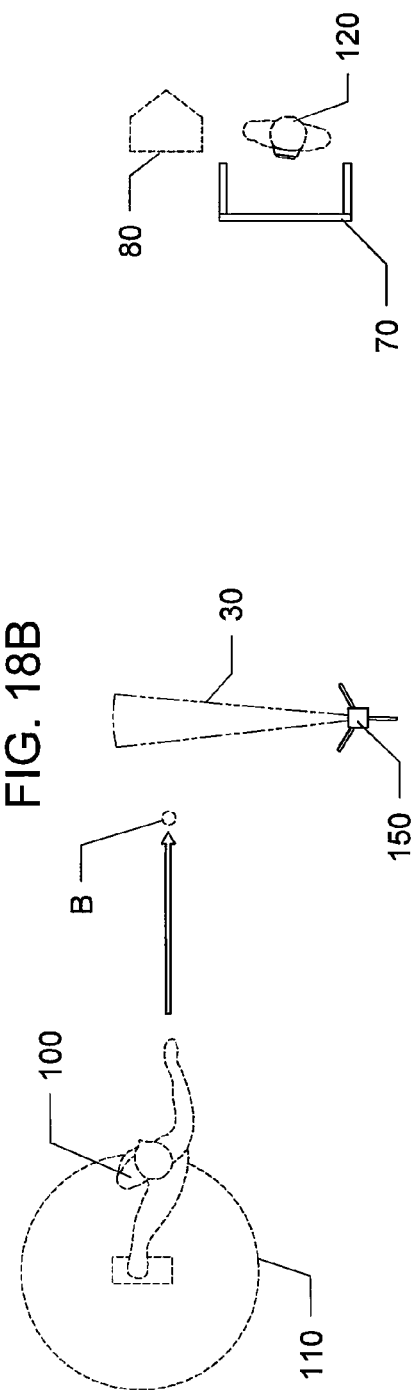

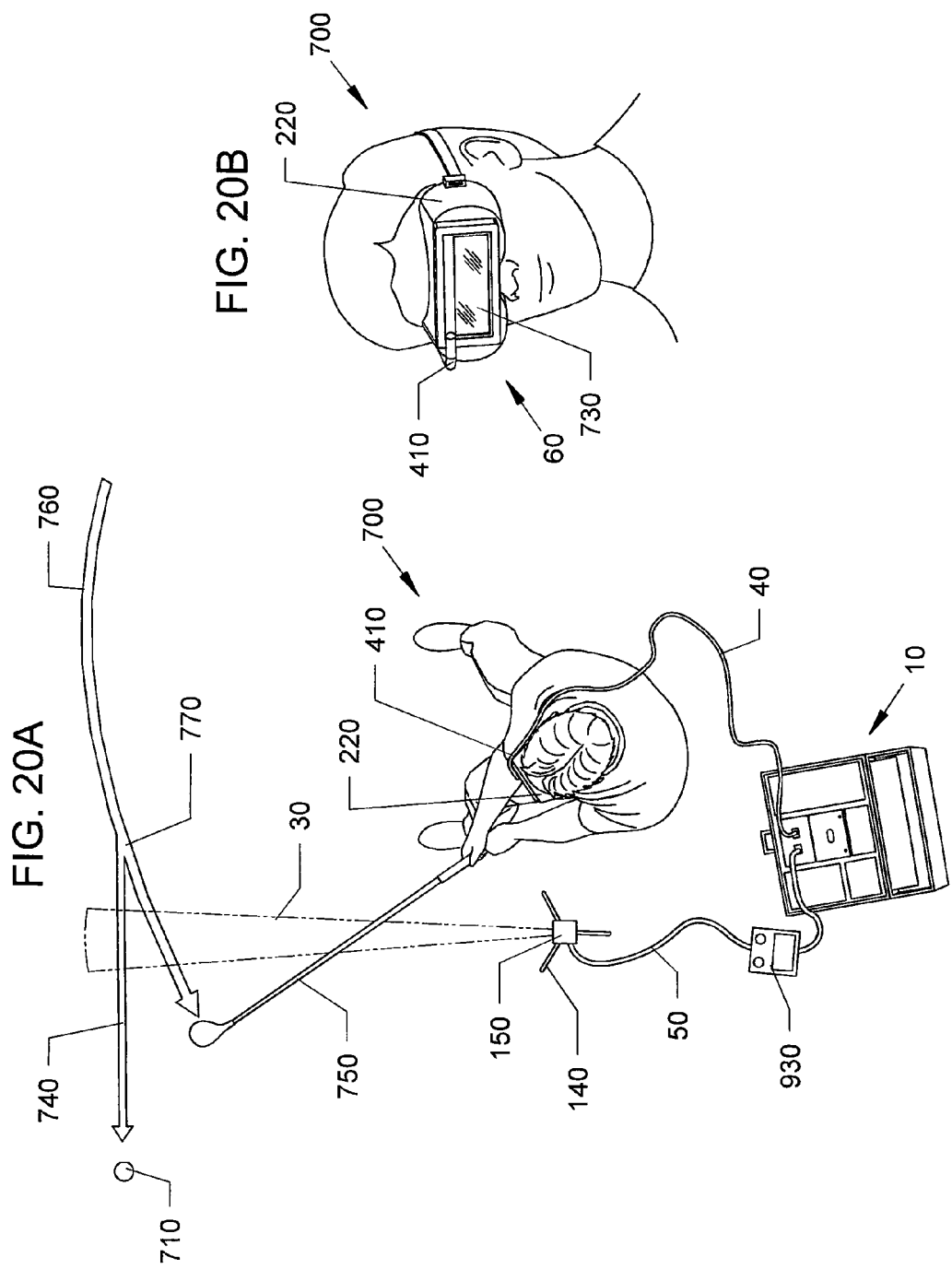

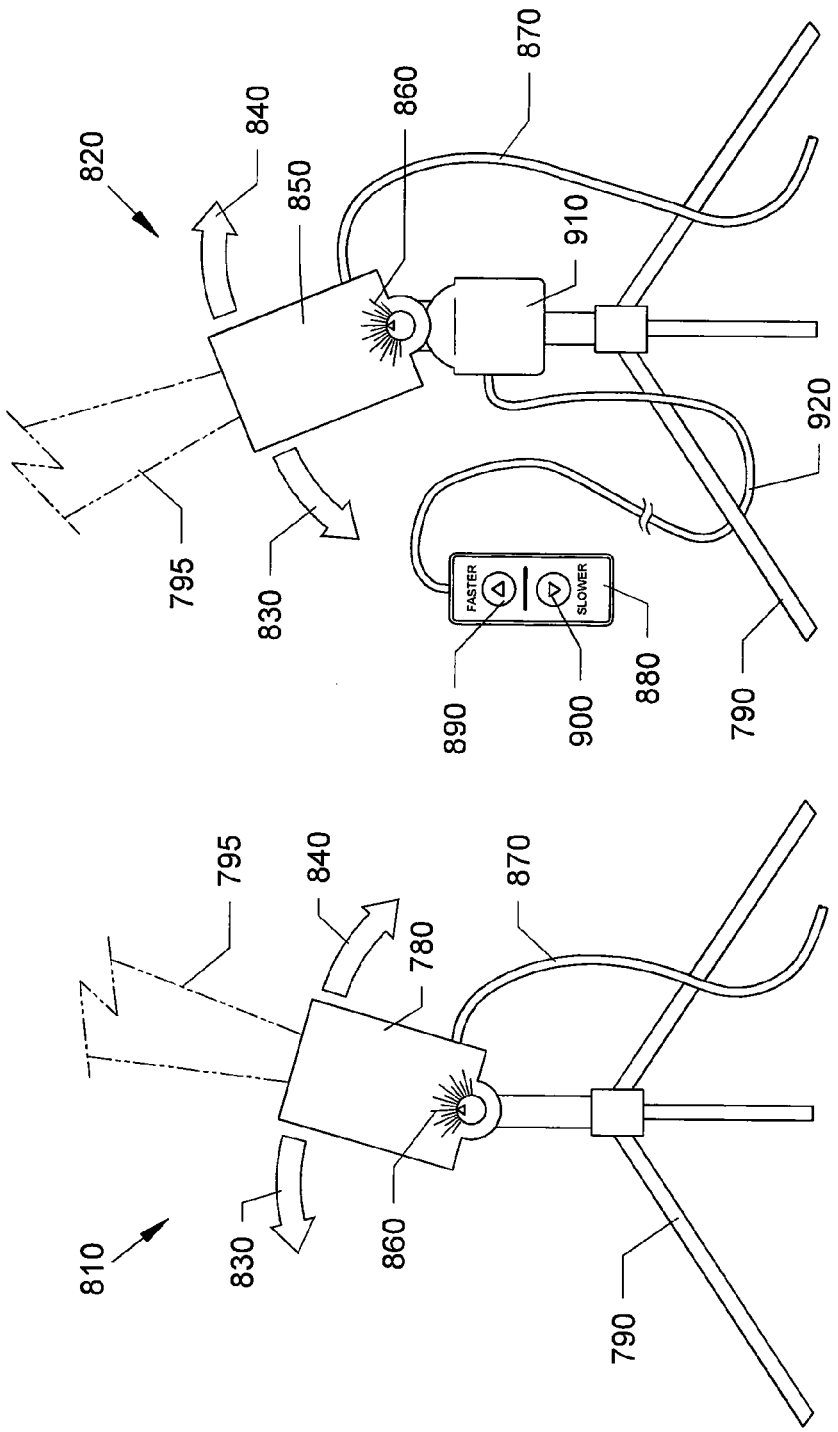

VISION TRAINING SYSTEM AND METHOD OF USE

CROSS REFERENCE TO RELATED APPLICATIONS

This application is a Continuation In Part of U.S. patent application Ser. No. 14/752,328 filed Jun. 26, 2015, now allowed, the entire disclosure of which is incorporated by reference in its' entirety.

FIELD OF INVENTION

This invention relates to training batters, and in particular to devices, apparatus, systems, and methods for training baseball and softball batters, to identify types (fastball, curveball, slider and changeup) of pitched balls and locations (strike or non-strike zone) of pitched balls in order to increase hitting accuracy.

BACKGROUND AND PRIOR ART

It is important for baseball hitters to identify not only the different types of pitches pitched by a pitcher but to also recognize if the pitched ball is going into the strike zone or ball zone in order to be successful.

Currently the most popular types of pitched balls include fastballs, curveballs, sliders, and changeups. Over time hitters develop favorite pitches to hit, and often find it desirable to swing only on those types of pitches. However, the batter has less than approximately one second to make this identification in order to determine the type of pitch being made.

The batter must also determine at the same time if the ball is being thrown in the strike zone or outside the strike zone and not worth hitting. Batters learning to hit a baseball need to be patient and look for a good pitch to hit and not waste a swing on a pitch that is not in the strike zone. Accordingly, what is needed is a system for training batters to swing only at strikes.

By example, a baseball exceeding about 82 mph travels at about 130 ft/sec and a pitched softball exceeding about 63 mph travels at about 100 ft/sec). Thus, the hitter as an extremely short period of time of less than approximately one second to determine if both the ball being pitched is a desired pitch (for example, fastball, curveball, slider or changeup), as well as determine if the pitched ball is in or outside the strike zone.

Various attempts have been made over the years to help the batter. For example, U.S. Pat. No. 4,303,241 to Burroughs describe a sports vision training device. However, this device requires components and setup that would not be desirable for regular repeated use. For example, Burroughs recommends using "plywood" boards on a pressure switch to activate the device, large painted face shields, and requires long cumbersome "cables" for being used on the baseball playing field. The use of these components would be difficult to setup, difficult to repetitively use over time for training different batters, and also would become a tripping hazard for players on the field. As such, this attempt is not practical for real world use on a baseball or softball field.

Thus, the need exists for solutions to the above problems with the prior art.

SUMMARY OF THE INVENTION

A primary objective of the present invention is to provide devices, apparatus, systems, and methods for training batters, such as baseball and softball batters to identify types and locations of pitched balls in order to increase hitting accuracy A secondary objective of the present invention is to provide devices, apparatus, systems, and methods for training batters, such as baseball and softball batters to identify as close as possible to when the pitcher is releasing the ball as to whether the pitched ball is a fastball, a curveball, a slider, or a changeup.

A third objective of the present invention is to provide devices, apparatus, systems, and methods for training batters, such as baseball and softball batters to recognize as close as possible when the pitcher is releasing the ball as to whether the pitched ball is in or out of a strike zone.

A fourth objective of the present invention is to provide devices, apparatus, systems, and methods for placing an artificial limitation on the amount of time and/or distance a hitter needs to view a thrown ball, in order to train the batter to increase their hitting accuracy.

A fifth objective of the present invention is to provide devices, apparatus, systems and methods for training and improving the accuracy of baseball and softball hitters to identify pitch types, pitch locations with or without changing pitched ball speeds with a portable system that can use wireless components.

Novel devices, apparatus, systems and methods are used to train a batter to better visually identify the types of pitched balls being released by a pitcher so that the batter can selectively swing at desired types of pitched balls. For example, the invention described herein conditions the batter to better concentrate at looking at the motion of the pitcher and pitched ball to identify if the pitched ball is a fastball, curve ball, slider or changeup, and to desensitize the user to the motion of balls that are not desired pitches and to other motions associated with a pitched ball such as the motion of the pitcher and the like which may distract the user.

Novel devices, apparatus, systems and methods are used to train a user to better visually recognize pitches that are strikes and to condition the user to hit good pitches and to not swing at pitches that are not strikes. For example, the invention described herein conditions the batter to better concentrate looking at the motion of the pitcher to look for motion to cause the pitched ball to go into the defined strike zones and to desensitize the user to the motion of balls that are not strikes and to other motions associated with a pitched ball such as the motion of the pitcher and the like which may distract the user.

A system for training golfers from looking up from a golf swing, can include a motion sensor that is adapted to be triggered by a swinging golf club, a black out lens adapted to be in front of a golfer being trained, and a control for changing the lens from transparent to opaque when a swinging golf club travels through a sensor path of the motion sensor.

The motion sensor can include a support for the motion sensor for generating an upwardly facing cone of sensitivity, wherein the motion sensor is adapted to be triggered when the swinging golf club travels through the cone of sensitivity of the motion sensor The system can include eyewear for supporting the blackout lens adapted to be worn by the golfer being trained.

The system can include a timer connected between the motion sensor and the black out lens for delaying the control for changing the lens from transparent to opaque.

A system for training baseball and softball batters, to identify types of pitched balls and locations (strike or non-strike zone) of pitched balls in order to increase hitting accuracy, can include a tiltable motion sensor that is adapted to be triggered with a pitched ball being sensed by the motion sensor, a black out lens adapted to be in front of a hitter being trained, and a control for changing the lens from transparent to opaque at selected distances the pitched ball travels from the release of the pitched ball to before the pitched ball reaches the hitter, wherein types of pitched balls and locations of pitched balls is identified.

The tiltable motion sensor can be adapted to be tilted toward the pitcher. The tiltable motion sensor can be adapted to be tilted toward the batter. The tiltable motion sensor can include a graduated tilt scale for manually adjusting the tiltable motion sensor. The tiltable motion sensor can include a motor for tilting the tiltable motion sensor in selected tilt angles. The tiltable motion sensor can include a remote control for activating the motor for tilting the tiltable motion sensor in the selected tilt angles.

A system for training batters constantly follow the path of a pitched ball and prevent the batters from looking up from a batting swing, can include a motion sensor that is adapted to be triggered by a pitched ball, a black out lens adapted to be in front of a pitcher being trained, and a control for changing the lens from transparent to opaque when the pitched ball travels through a sensor path of the motion sensor adapted for when the pitched ball is passing the batter. The motion sensor can include a support for the motion sensor for generating a cone of sensitivity, wherein the motion sensor is adapted to be triggered when the pitched ball travels through the cone of sensitivity of the motion sensor. The motion sensor can include a support for the motion sensor for generating a fan emission of sensitivity, wherein the motion sensor is adapted to be triggered when the pitched ball travels through the fan emission of sensitivity of the motion sensor The system can include eyewear for supporting the blackout lens adapted to be worn by the batter being trained, and a protective shield adapted to be in front of the batter.

Further objects and advantages of this invention will be apparent from the following detailed description of the presently preferred embodiments which are illustrated schematically in the accompanying drawings.

BRIEF DESCRIPTION OF THE FIGURES

FIG. 2 is a perspective view of the system setup shown in FIG. 1.

FIG. 6A is a perspective view of the tripod from FIG. 5 in a deployed position.

FIG. 6B shows the tripod of FIG. 6A with the tripod legs folded.

FIG. 6C shows the tripod of FIG. 6A with the tripod disassembled.

FIG. 9 is a perspective view of an alternate embodiment flip-door goggle embodiment with electromagnet actuation.

FIG. 10 is another perspective view of the alternative goggles of FIG. 9 with the door shown down.

FIG. 13 is a perspective view of another embodiment of the blackout goggle with no IR sensor.

FIG. 14 is a perspective view of still another embodiment of the blackout goggle with no IR sensor.

FIG. 17 is a pitch chart used to tabulate and evaluate the training subject's progress.

FIG. 18A is a side view of a configuration of the invention with a variable placement of the motion sensor.

FIG. 18B is a top view of a configuration of the invention with a variable placement of the motion sensor of FIG. 11A.

FIG. 20A is an updated view of FIG. 19A showing the path of the golf club and the path of the golf ball just after the club has made contact with the ball.

FIG. 20B is a front perspective view of the blackout goggles of FIG. 19B showing that the view screen is blacked out after the club passes through the motion sensor cone.

FIG. 22 is an enlarged side view of a configuration of a manually adjustable tilting, upward looking sensor assembly, with a graduated tilt scale on the side.

FIG. 23 is an enlarged view of the tiltable sensor assembly of FIG. 22 with the addition of a motor to adjust the tilt and a remote control to control the motor.

DESCRIPTION OF THE PREFERRED EMBODIMENTS

Figure 1:
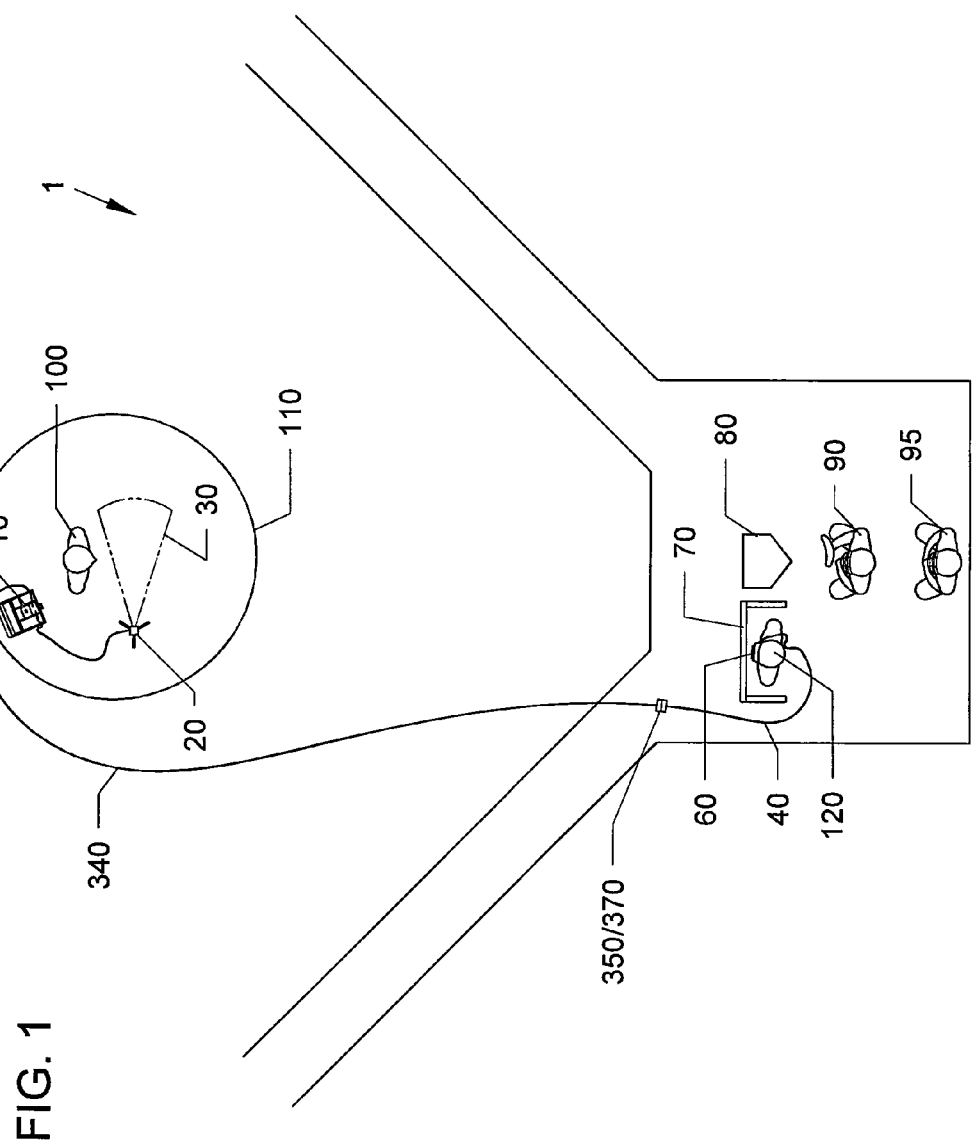
FIG. 1 is a top plan view of a system setup of the invention on a baseball playing field.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification does not include all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

A list of components will now be described.

1 system setup on a baseball field
10 Portable vision training system in carrying case.
20 Tripod Assembly with Motion sensor mounted on tripod.
30 Motion sensor "cone" (beam array) of sensitivity.
40 Infra Red (IR) cable
50 Cable from motion sensor plugs to receptacle in case.
60 Blackout assemblies (goggle assembly) with goggles 220 and IR light assembly 230 mounted. The training subject 120 looks through glass, W, that is normally clear but will "blackout" when exposed to IR light 400.
70 Protective shield for training subject (hitter)
80 Home plate.
90 Catcher.
95 Observer/umpire
100 Pitcher.
110 Pitchers mound.
120 Training subject (batter)
130 Carrying case for vision training system.
140 Tripod for mounting motion sensor. Legs can be folded and retracted for storage.
150 Motion sensor.
160 Rechargeable battery.
170 Battery cover.
180 A.C. Powered battery charger.
190 On/off switch.
200 Goggle receptacle.
210 Motion sensor receptacle.
220 Blackout welding goggles.
230 IR light assembly with goggle cable and plug for receptacle.
with fasteners, adhesive, VELCRO (hook and loop fasteners).
240 Tripod adapter tube mounts motion sensor to adapter cap.
250 Tripod adapter cap mounts adapter tube to tripod.
260 Plug on motion sensor cable plugs to receptacle in case.
270 System control box.
280 Battery charging terminals.
290 Alligator clips on batter charger wires clip to charging terminals.
300 Cavity for tripod assembly storage.
310 Cavity for goggle assembly storage.
320 Cavity for battery charger storage.
330 Cavity for IR extension cable storage.
340 Extension cable for connecting the male IR cable from the goggles to the goggle receptacle in the case.
350 Female plug of IR extension cable plugs to male plug on IR cable from goggles.
360 Male plug of IR extension cable plugs to goggle receptacle in case.
370 Male plug of goggle IR cable plugs to female plug of IR extension cable.
380 Hex nut secures tripod adapter cap to tripod.
390 IR sensor is part of the welding goggles.
400 IR light is positioned such that it is shining on the IR sensor when mounted to the goggles.
410 IR light package.
420 Alternate embodiment goggles have a hinged opaque door
430 Flip-door style welding goggles.
440 Magnet cable connecting the electromagnet to the extension cable which then connects to the carrying case.
450 Male plug on the magnet cable connects to the female plug on the extension cable.
460 Electromagnet.
470 Electromagnet mounting plate can be removed via wing nuts from the goggles for storage.
480 Wing nuts secure the electromagnet mounting plate to the goggles.
490 Bracket permanently attached to the goggles adapts the electromagnet mounting plate.
500 Hinged flip-up door is supplied with the goggles.
510 Steel "puck" (strike plate) is affixed to the flip-up door via a bracket. The puck provides the electromagnet with a holding point for the door.
520 Bracket for mounting the steel puck to the flip-up door.
530 Screws on goggle bracket provide mounting points for the electromagnet mounting plate.
540 Mounting hardware for goggle bracket.
550 Mounting hardware for steel puck bracket.
560 Alternate embodiment blackout goggles using no IR light or IR sensor.
570 Cable connecting goggles to carry case.
580 Male plug connects to female receptacle in carry case.
590 Alternate embodiment blackout goggles using no IR light, IR sensor, or hard cable connecting the goggles to the carry case.
600 Cable connecting goggles to wireless receiver.
610 Wireless receiver.
620 Clip on wireless receiver for the training subject can clip the receiver to his clothing.
700 Golfer.
710 Golf ball.
720 Lens clear.
730 Lens dark.
740 Golf ball path.
750 Golf club.
760 Golf club path.
770 Club-ball contact point.
780 Tilting, upward facing sensor.
790 Tripod for tilting sensor.
795 Upward pointing motion sensor cone.
800 Batter.
810 Tilt sensor assembly. Manually adjustable.
820 Tilt sensor assembly. Remotely adjustable.
830 Faster/sooner sensor rotation direction.
840 Slower/later sensor rotation direction.
850 Tilting sensor, remote controlled.
860 Graduated tilt scale.
870 Cable from sensor to system case.
880 Tilt motor remote control.
890 Faster/slower remote control button.
900 Slower/later remote control button.
910 Sensor tilt motor.
920 Remote control cable.

930 Optional timer between motion sensor and I.R. sensor on goggles. This timer can be used in any configuration of this system.

For pitching baseballs, a pitcher can often pitch balls over the plate between low ranges of less than approximately 45 miles per hour to higher range of approximately 102 miles per hour.

For children up to 12 years of age baseball fields typically have a distance between the pitcher's mound and home plate of approximately 45 feet.

After 12 years of age, typically high school, college, semi pro and professional baseball fields have a distance between the pitcher's mound and home plate of approximately 60.5 feet.

Typically, the time between the times a pitched ball leaves a pitchers hand to the time the ball crosses the plate can be no more than approximately 6/10 of a second.

Table 1 shows a reaction time in seconds based on balls being pitched in miles per hour along two foot increment distances of 40 and 60 feet between the pitching mounds (for pitchers) and home plate (for hitters).

TABLE 1

Reaction Time in Seconds

| | DISTANCE (feet) | | | | | | | | | | |
|---|---|---|---|---|---|---|---|---|---|---|---|
| MPH | 40 | 42 | 44 | 46 | 48 | 50 | 52 | 54 | 56 | 58 | 60 |
| 66 | 0.41 | 0.43 | 0.45 | 0.48 | 0.50 | 0.52 | 0.54 | 0.56 | 0.58 | 0.60 | 0.62 |
| 68 | 0.40 | 0.42 | 0.44 | 0.46 | 0.48 | 0.50 | 0.52 | 0.54 | 0.56 | 0.58 | 0.60 |
| 70 | 0.39 | 0.41 | 0.43 | 0.45 | 0.47 | 0.49 | 0.51 | 0.53 | 0.55 | 0.56 | 0.58 |
| 72 | 0.38 | 0.40 | 0.42 | 0.44 | 0.45 | 0.47 | 0.49 | 0.51 | 0.53 | 0.55 | 0.57 |
| 74 | 0.37 | 0.39 | 0.41 | 0.42 | 0.44 | 0.46 | 0.48 | 0.50 | 0.52 | 0.53 | 0.55 |
| 76 | 0.36 | 0.38 | 0.39 | 0.41 | 0.43 | 0.45 | 0.47 | 0.48 | 0.50 | 0.52 | 0.54 |
| 78 | 0.35 | 0.37 | 0.38 | 0.40 | 0.42 | 0.44 | 0.45 | 0.47 | 0.49 | 0.51 | 0.52 |
| 80 | 0.34 | 0.36 | 0.38 | 0.39 | 0.41 | 0.43 | 0.44 | 0.46 | 0.48 | 0.49 | 0.51 |
| 82 | 0.33 | 0.35 | 0.37 | 0.38 | 0.40 | 0.42 | 0.43 | 0.45 | 0.47 | 0.48 | 0.50 |
| 84 | 0.32 | 0.34 | 0.36 | 0.37 | 0.39 | 0.41 | 0.42 | 0.44 | 0.45 | 0.47 | 0.49 |
| 86 | 0.32 | 0.33 | 0.35 | 0.36 | 0.38 | 0.40 | 0.41 | 0.43 | 0.44 | 0.46 | 0.48 |
| 88 | 0.31 | 0.33 | 0.34 | 0.36 | 0.37 | 0.39 | 0.40 | 0.42 | 0.43 | 0.45 | 0.46 |
| 90 | 0.30 | 0.32 | 0.33 | 0.35 | 0.36 | 0.38 | 0.39 | 0.41 | 0.42 | 0.44 | 0.45 |
| 92 | 0.30 | 0.31 | 0.33 | 0.34 | 0.36 | 0.37 | 0.39 | 0.40 | 0.42 | 0.43 | 0.44 |
| 94 | 0.29 | 0.30 | 0.32 | 0.33 | 0.35 | 0.36 | 0.38 | 0.39 | 0.41 | 0.42 | 0.44 |
| 96 | 0.28 | 0.30 | 0.31 | 0.33 | 0.34 | 0.36 | 0.37 | 0.38 | 0.40 | 0.41 | 0.43 |
| 98 | 0.28 | 0.29 | 0.31 | 0.32 | 0.33 | 0.35 | 0.36 | 0.38 | 0.39 | 0.40 | 0.42 |
| 100 | 0.27 | 0.29 | 0.30 | 0.31 | 0.33 | 0.34 | 0.35 | 0.37 | 0.38 | 0.40 | 0.41 |
| 102 | 0.27 | 0.28 | 0.29 | 0.31 | 0.32 | 0.33 | 0.35 | 0.36 | 0.37 | 0.39 | 0.40 |

FIG. 1 is a top plan view of a system setup 1 of the invention on a baseball playing field. FIG. 2 is a perspective view of the system setup 1 shown in FIG. 1.

Figure 4:
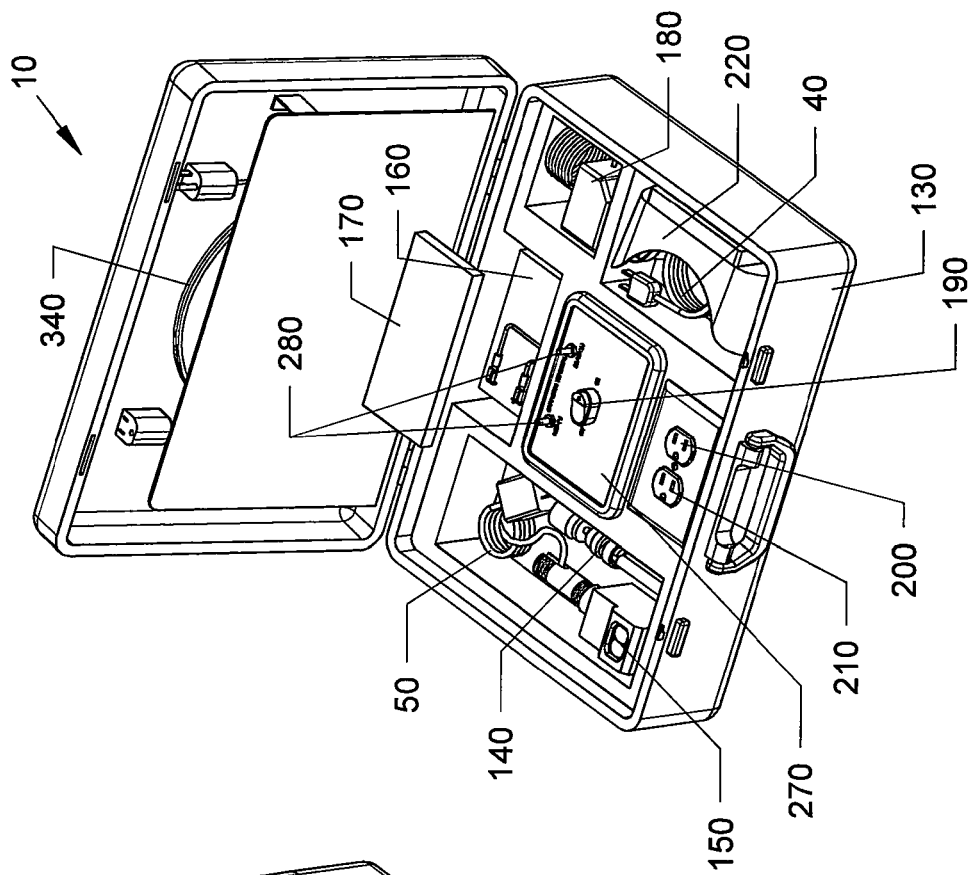
FIG. 4 is another perspective view of the case of FIG. 3 in an open position and the battery cover lifted to show the battery.
Figure 3:
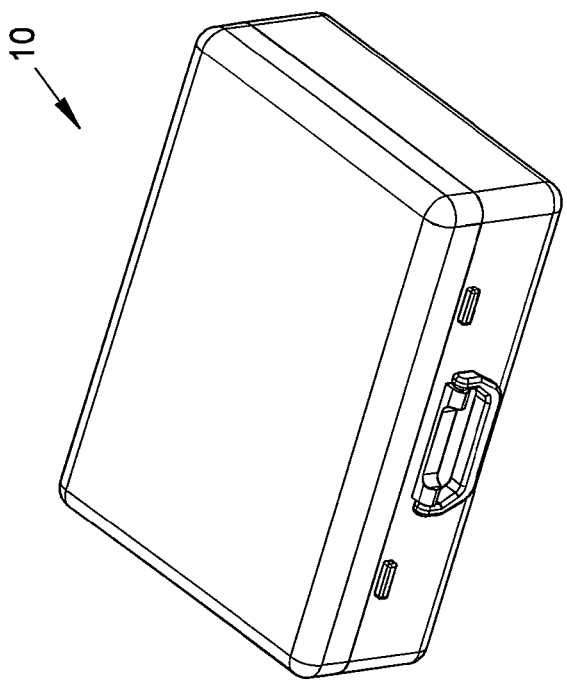
FIG. 3 is a perspective view of a portable visions training system in a portable case with the case closed.
Figure 5:
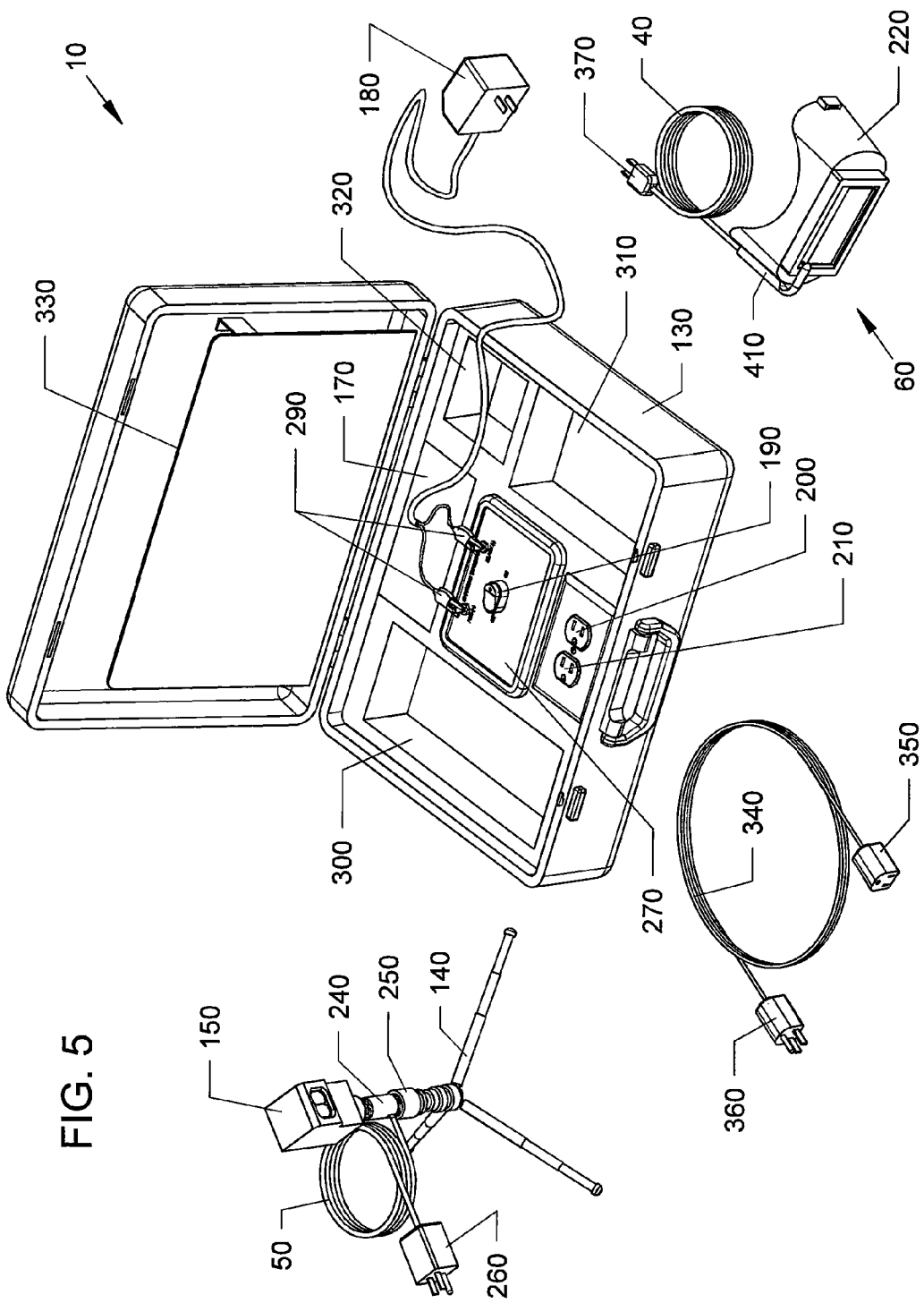
FIG. 5 is another perspective view of the case of FIG. 4 with the components removed and the battery charger is clipped to the charging posts on the system control box.

FIG. 3 is a perspective view of a portable visions training system of the setup components 1 in a portable case 10 with the case 10 closed. FIG. 4 is another perspective view of the case 10 of FIG. 3 in an open position and the battery cover 170 lifted to show the battery 160. FIG. 5 is another perspective view of the case 10 of FIG. 4 with the components removed and the battery charger 180 is clipped to the charging posts (battery charging terminals 280) with alligator clips 290 on the system control box 270, and on and off switch 190. The motion sensor 150 has been mounted to its tripod 140. Case 130 can include a cavity 300 for tripod assembly 20 storage, a cavity 310 for goggle assembly 60 storage, cavity 320 for battery charger 180 storage, cavity 330 for IR extension cable 340 storage.

FIG. 6A is a perspective view of the motion sensor on tripod 20 from FIG. 5 with tripod 140 legs in a deployed position. FIG. 6B shows the motion sensor on tripod 20 of FIG. 6A with the tripod 140 legs in a folded position. FIG. 6C shows an exploded view of the motion sensor on tripod 20 of FIG. 6A with the tripod disassembled. Motion sensor 150 can be connected to cable 50, which has a plug 260 at one end. The bottom of motion sensor 150 can be attached to a tripod adapter tube 240. The top of tripod 140 legs can have a threaded end which passes through tripod adapter cap 250, and is held in place by a hex head nut 380, which secures the tripod adapter cap 250 to the tripod 140.

Figure 7:
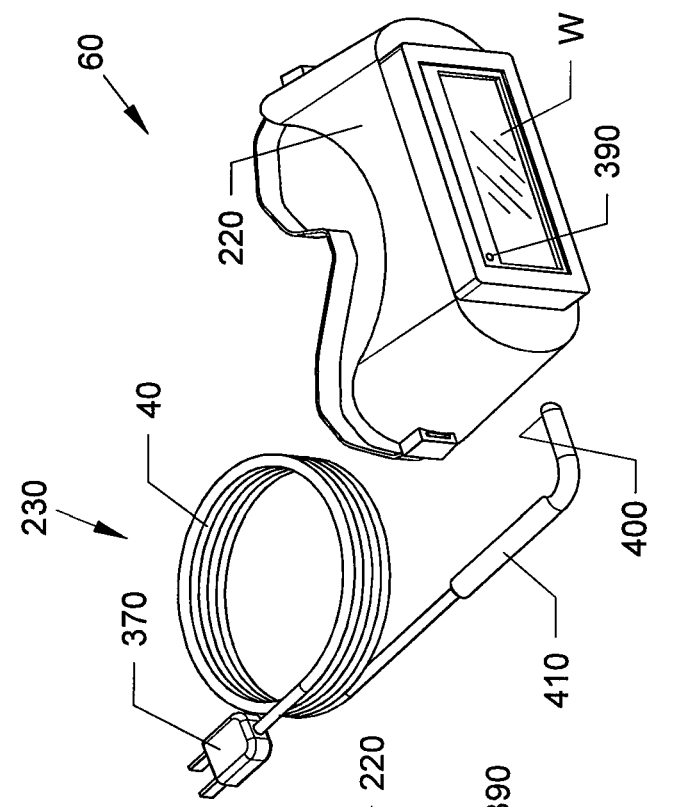
FIG. 7 is a perspective view of the IR (infrared) blackout goggles with the IR emitter package mounted.

FIG. 7 is a perspective view of the IR (infrared) blackout goggles 60 with the IR emitter package mounted. The goggles lens is normally transparent. When the IR emitter shines on the IR sensor of the goggles, the lens becomes opaque.

Figure 8:
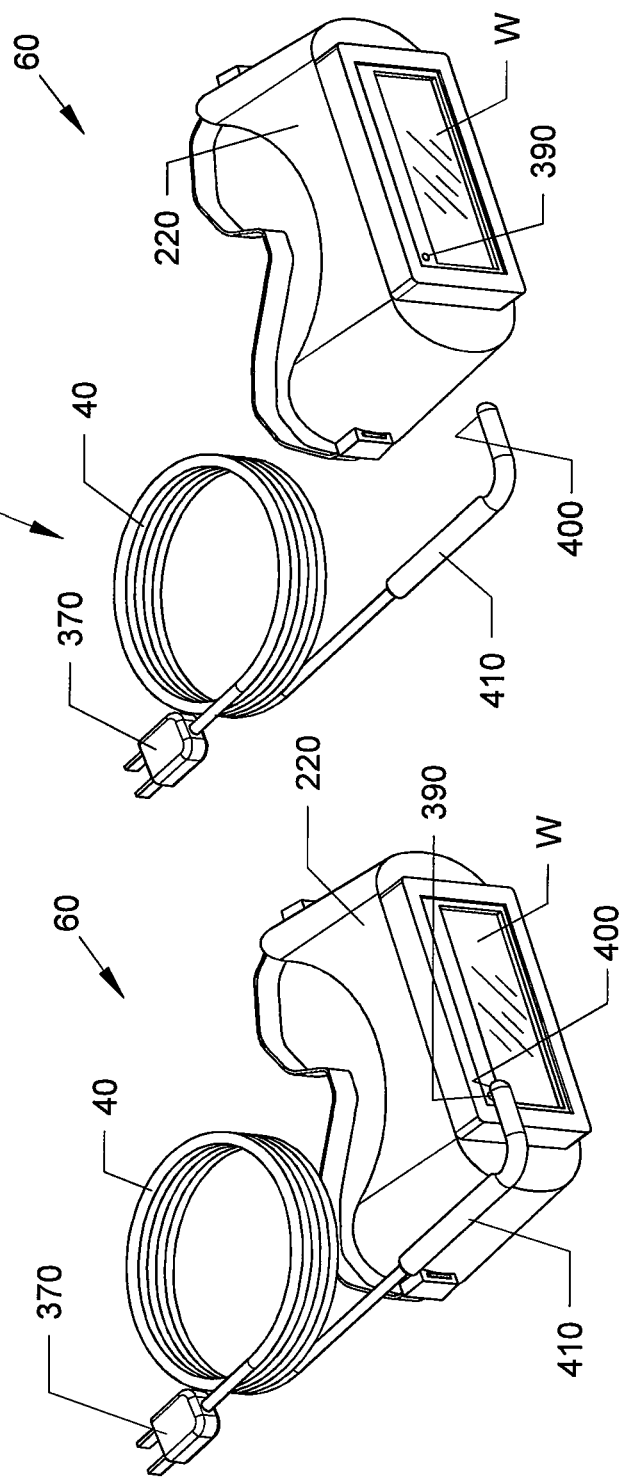
FIG. 8 is a perspective view of the goggles of FIG. 7 with the IR emitter package disassembled.

FIG. 8 is a perspective view of the goggles 60 of FIG. 7 with the IR emitter package disassembled.

Referring to FIGS. 1-8, the setup 1 can include the portable vision training system 10 in carrying case 130, with the motion sensor arrangement 20 of the motion sensor 150 on the tripod 140, with the motion sensor 150 having a "cone" of sensitivity 30 all about a pitcher 100 on a mound 110. An Infra Red (IR) cable 40 plugs to a receptacle 200 in the case 130. At the end of the IR light assembly 230 opposite the plug 370 is affixed a package 410 that contains an IR light 400. This IR light package 410, when mounted, is positioned such that IR light 400 shines on an IR sensor 390 that is part of the welding goggles 220. When the IR light 130 from the package 410 is sensed by the IR sensor 390 on the goggles 220 the window, W, in the goggles 220 goes from transparent to opaque. IR cable 40 can be attached to extension cable 340 by female plug 35 and male plug 370. Male plug 360 of IR extension cable 340 plugs into goggle receptical 200 in case 130

Cable 50 from motion sensor 150 plugs to receptacle 210 in case 130. Black out assembly 60 includes black out goggles 220 with IR light package 410 mounted. The test subject (batter) 120 can look through the glass (lens)/window W, that is normally clear, in the goggles 220, but will black out when exposed to IR light 400.

In addition to a pitcher 100, there can be a training subject (batter) 120 that is next to home plate 80, with a catcher (observer) 90 behind the plate 80. During use, the training subject (batter) 120 is wearing black out assembly 60 which includes the goggles 220 with IR light package 410. During operation, the training subject (batter) 120 can be standing behind a protective shield 70 that is used during the training of training subject (batter) 120. The protective shield can have a transparent surface, such as hurricane resistant glass, and the like, that allows the training subject (batter) 120 to see through the shield to see the balls being pitched, while protecting the training subject (batter) 120 from being hit and injured by a pitched ball from the pitcher 100.

Referring to FIGS. 1-8, the setup 1, can include three main components: 1) a motion sensor 20 with an integrated adjustable timer relay chip, 2) a power source (in this case, a 12 volt rechargeable battery 160) and 3) a lens and goggle combination assembly 60, wherein the lens, W, can be activated to change from clear to opaque upon energizing an Infrared Emitter, (i.e. an auto-darkening lens).

Motion Sensor 20—The motion sensor 150 in the motion sensor assembly 20 can be equipped with a 5-wire cable. The motion sensor 150 being used can be, but is not limited to a Model# Q45VR3DL by BANNER Engineering Corporation, which can be a one-piece photoelectric sensor that an be placed in the vicinity (within approximately 6') of the lead foot of the pitcher 100 as the triggering mechanism for the process to start the auto darkening of the lens W, in the goggles 60. The motion sensor 150 can be equipped with a timing chip, such as but not limited to a Model 45LM Series Modules by BANNER Engineering Corporation that can be adjusted manually by a 15-turn screw.

Each of the 5 wires is a different color, signifying its purpose. Two of the wires are directed to the power source 160, 2 wires are directed to the Infrared Emitter, 400, and the 5$^{th}$ wire is not used.

Power Source 160—The power source 160 can be a commercially available 12 volt rechargeable battery.

Lens/Goggle Combination 60—The goggles 220 can be a commercially available welder's goggle, such as goggles with liquid crystal display lens, with a 2"×4" opening for the lens, W. For example, PYRAMEX model WHA200 welding goggles with sensors, and the like, can be used. The lens, W, can have an auto darkening feature that, when the Infrared Emitter 400 is energized above the Infrared Sensor of the goggles, causes the lens W to become opaque for 2 seconds. Other types of liquid crystal type displays can be used such as but not limited to ones used with eye glasses, helmets, and the like.

The integration of the above components is as follows:
1. The motion sensor 20 can be connected to the power supply 160 and the Infrared Emitter, 400, through cables, 340, 40 (or wirelessly).
2. The Infrared Emitter 400, can be connected to the motion sensor 20 and the power supply 160 through cables (or wirelessly)
3. The power source 160 can be connected to both the motions sensor 20 and infrared emitter 400, thereby closing the circuit.

The system can function and operate in an outdoor environment or indoors, and can include a system setup and system placement.

The environment that this system can be utilized can include but is not limited to a baseball or softball playing field, and the like. For example, the pitcher's mound 110 to home plate 80 whether on the actual playing field, bullpen or setting of similar nature.

The system set up can operate as follows:
1. Plug the cord of the motion sensor 20 into the appropriate outlet
2. Plug the short cord of the Infrared Emitter 400 into the plug of the long cord
3. Plug the long cord into the appropriate outlet
4. Attach the Infrared Emitter 400 to the goggles 60 making sure the Emitter 400 is placed directly over the sensor 390 on the lens, W
5. Energize the system.

System Placement—

The placement of the individual components can be as follows:

Motion Sensor 20—The motion sensor 20 can be placed in a location where it can read the movement of the lead foot of the pitcher 100 when it lands. The motion sensor 20 can have a range of up to approximately 6 feet. However, signal strength is more consistent between approximately 2 feet to approximately 4 feet. The 2 primary factors in determining the placement of the motion sensor 20 can be 1) receiving a strong consistent signal from the motion sensor 20 and 2) not interfering with the mechanics of the pitcher 100.

Infrared Emitter/Goggles 60—The goggles 220 with the Infrared Emitter (IR light assembly 230) can be placed on the head of the batter 120. The batter 120 would then stand next to home plate 80 in the same manner as he/she would prepare to hit. Due to the defenseless nature of the hitter 120, it is important for safety concerns that the hitter 120 be behind a protective screen 70.

Power Source 160—The power source 160 can be placed anywhere as long as it does not interfere with the pitcher 100 or hitter 120.

System Function—When the lead foot of the pitcher 100 crosses the zone of influence 130 of the motion sensor 20, the motion sensor 20 can send a signal to the timer relay chip that can be used with the motion sensor 150. The timer relay chip will receive the signal and, per a predetermined delay, will then energize the infrared emitter for a predetermined amount of time. The energized emitter in the IR light assembly 230 can send an infrared light wave 400, 410 that is captured by the sensor 390 on the lens W. The internal components of the lens W can then cause the lens W, to darken in approximately 1/24,000 of a second and remain dark for approximately 2 seconds.

The delay by the timer relay chip in the motion sensor 150 can be adjusted from approximately 0.001 seconds to approximately 15 seconds. The range appropriate for use in this system should be from approximately 0.1 seconds to approximately 0.7 seconds, which is well within the functionality of this timer relay.

Purpose of System

First, the purpose of the system can be based on the following premises:
1. To be successful, the hitter must know the type of pitch (fastball, curve ball, slider and changeup) and the location of said pitch (whether in or out of the strike zone.
2. The trajectories of the 4 most common pitches (fastball, curveball, slider and changeup) are fairly predictable.
3. By recognizing the pitch type and location (in and out of the strike zone) earlier in the trajectory, the hitter 120 gains an advantage.

Therefore, based on these premises, the purpose of the system is to place artificial limitations on the amount of time and/or distance that the hitter 120 can view the object, being the ball. By doing so the hitter 120 can be forced to process the details of each pitch with less information. Through repetition and feedback (discussed below), the hitter should be able to decrease the amount of time needed to determine a pitch type and location, thereby, giving the hitter more time to swing or not swing at the pitch.

Use of System

This system can be utilized in is a baseball or softball setting, specifically, the pitcher's mound to home plate whether on the actual playing field, bullpen or setting of similar nature. Four participants are required. They are as follows:

1. Pitcher 100
2. Catcher 90
3. Hitter (person being trained) 120
4. Observer (umpire) charting pitches 95

The pitcher 100, catcher 90 and hitter 120 can assume their natural positions with the exception that the hitter 120 can have a protective screen 70 placed between him/her 120 and the pitcher 100 for safety precautions. The observer 95, such as an umpire (will either or both position him/herself in a location where they can both verbally hear the hitter and visually see the entire trajectory of the thrown pitch.

The observer can have a chart with ten 5×5 grids signifying the 25 most probable locations of each pitch. The inner 3×3 grid represent the 9 zones of a strike (inside, middle, outside by upper, middle, lower). The remaining exterior zones represent balls thrown outside of the strike zone.

After the timer relay chip has been set to the desired delay, the pitcher will begin throwing pitches to the catcher in a normal manner. For each pitch, the hitter will call out the pitch type, vertical and horizontal location of where the ball will cross home plate and whether ball is a strike or ball (i.e. "fastball, low and away, ball", "curveball up and in, strike"). The observer 95 can note the pitch type and location on the 5×5 grid called out by the hitter which will be described in reference to FIG. 17. The observer 95 can then note on the same 5×5 grid the actual pitch type and location.

After a determine number of pitches, the hitter 120 and observer 95, can compare their results and a percentage will be tallied for the hitter for correctly calling both of the following:

Pitch type (fastball, curveball, slider and changeup)
Location of each pitch (in or out of strike zone)

Once the hitter 120 can successfully and consistently call out the correct pitch type and location, the delay in the timer relay can be decreased. The procedure is then repeated until the hitter can, again, successfully and consistently call out the correct pitch type and location.

For example where the distance between home plate 80 and the mound 110 is 60 feet, the lens, W in the goggles 60 on the hitter 120 can be blacked out starting at a distance of 50 feet from the pitcher's mound 110.

The training can have the hitter needing to successfully identify both the pitch type and location of the pitch in 8 or 9 out of 10 pitched balls from the pitcher 100. Once a success rate of 8 or 9 out of 10 pitches occurs, the invention can blacken out the lens, W in a 10 foot increment. So the lens W on the goggles 60 can be blacked out when the pitched ball is at 40 feet from the pitcher's mound. Again, the hitter 120 would need to keep trying to identify pitch type and pitch location, and would need to keep identifying both until an 8 or 9 out of 10 success rate is achieved. The aim is to keep moving back the blacken lens, W, effect until and as close to the pitcher's release of the ball is achieved.

Benefits of Using System

1. This system can determine when a hitter 120 is actually reading the details of the pitch. If the hitter 120 is using too much time to determine the pitch type and location, he/she has less time to determine whether to swing or not.
2. By using this system in a repetitious manner, it is possible for the hitter 120 to process the information of each pitch quicker, thereby giving the hitter 120 more time to determine whether to swing or not.
3. If the hitter 120 is not making progress in processing the pitch information, it could signify an issue with the visual acuity of the hitter 120 that had previously been undetected.

FIG. 9 is a perspective view of an alternate embodiment flip-door goggle embodiment 420 with electromagnet actuation. Here, flip door welding goggles 430 can be used. A hinged opaque door 500 can be held out of the training subjects 120 line of sight by an electro magnet 460. At a signal from the motion sensor 20 (routed through the carrying case 130), the electromagnet 460 can release the hinged door 550 and occludes the training subject's 130 line of sight. The door 500 is shown up in this figure so that the training subject 130 could see if he was wearing the goggles 430.

FIG. 10 is another perspective view of the alternative goggles 420 of FIG. 9 with the door 500 shown down. In this Figure, the training subject 120 could not see if wearing the goggles 420.

Figure 11:
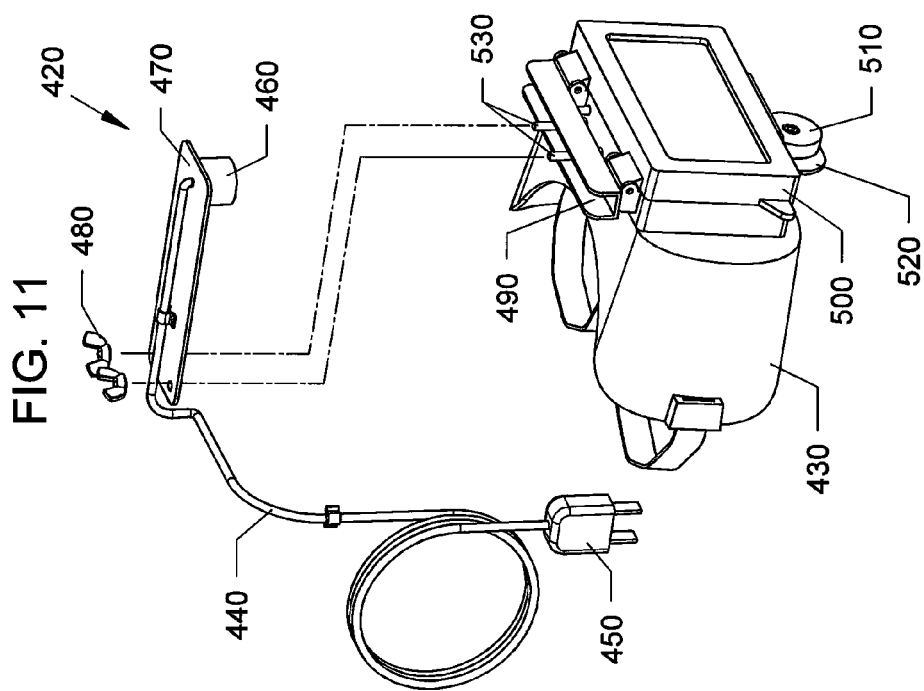
FIG. 11 is another perspective view of the goggles of FIG. 10 showing the electromagnet and cable removed for storage.

FIG. 11 is another perspective view of the alternative goggles 420 of FIG. 10 showing the electromagnet 460 and cable 440 removed for storage.

Figure 12:
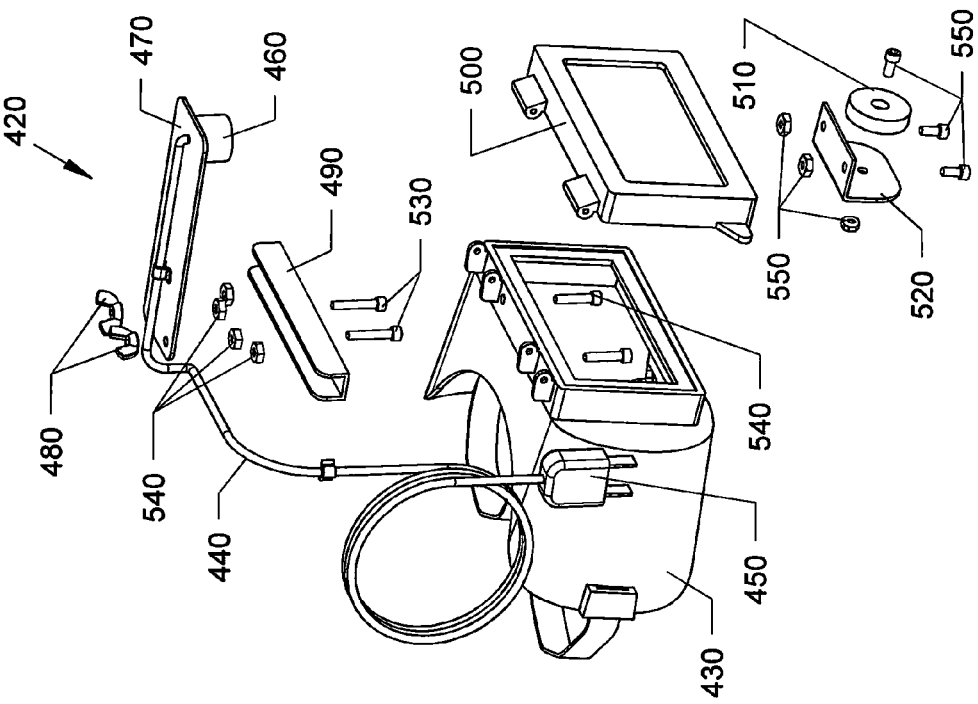
FIG. 12 is an exploded view of the goggles of FIG. 11 with the components identified.

FIG. 12 is an exploded view of the alternative goggles 420 of FIG. 11 with the components identified.

Referring to FIGS. 9-12, the alternative goggles 420 can include magnet cable 440 for connecting the electromagnet 460 to the extension cable 440 by a electromagnet mounting plate 470, that can be removed via wing nuts 480 from the goggles 430 for storage. A bracket 490 can be permanently attached to the goggles 430 adapts the electromagnet mounting plate 470.

Alternative goggles 420 can include a steel "puck" (strike plate) 510 that can be affixed to the flip-up door 500 via a bracket 520. The puck 510 can provide the electromagnet 460 with a holding point on the door 500. Fasteners 530, such as screws and bolts on goggle bracket 490 can provide mounting points for the electromagnet mounting plate 470. Mounting hardware 540, such as nuts, can be used with the fasteners 530 for the bracket 490. Additional mounting hardware 550 such as nuts, can be use with the fasteners 550 for the bracket 520 which mounts the steel puck 510 to the flip-up door 500.

The opposite end of the cable 440 can include a male plug 450 that can connect to the female plug on the extension cable 340 previously described.

FIG. 13 is a perspective view of another embodiment 560 of the blackout goggled with no IR sensor, and no IR light. This embodiment 560 can have the cable 570 with male plug 580 that connects to a female receptical in the carrying case 130 so that the system is wired directly into the goggles blackout lens W.

FIG. 14 is a perspective view of still another embodiment of the blackout goggle with no IR sensor, no IR light, or hard cable connecting the goggles to the carry case 130. A cable 600 can connect the goggles 590 to a wireless receiver 610, that the training subject 120 wears on his person. A wireless transmitter (not shown) in the carry case 130 can send a signal to the receiver 610 when the blackout lens W, needs to go dark. A clip 620 on the wireless receiver 610 can clip the receiver 610 to the clothing of the training subject 120.

Figure 15:
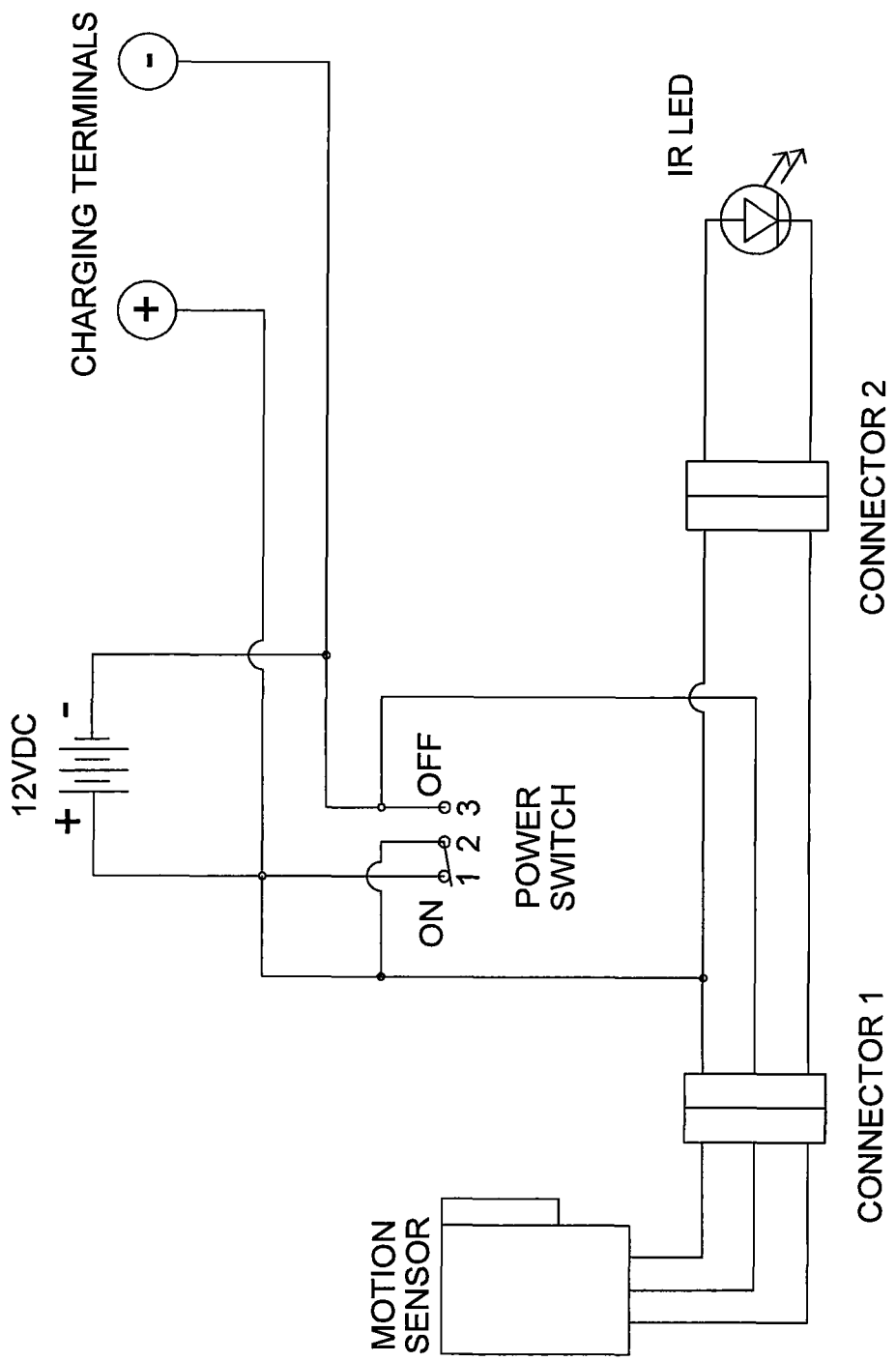
FIG. 15 shows a schematic of the components used in the IR emitter system.

FIG. 15 shows a schematic of the components used in the IR emitter system 1 used in the previous Figures.

Figure 16:
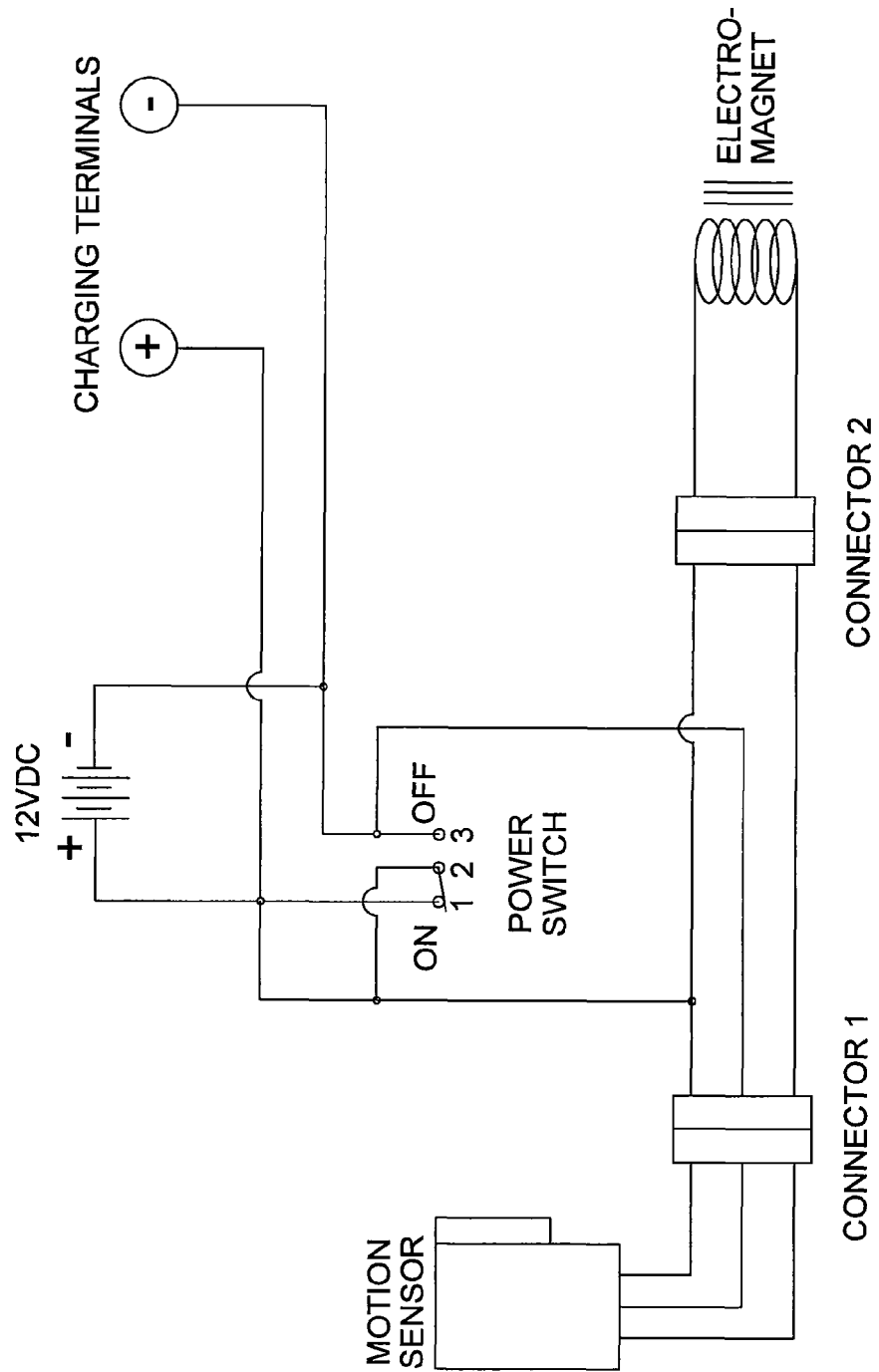
FIG. 16 shows another schematic of the components used in the electromagnet actuation system.

FIG. 16 shows another schematic of the components used in the electromagnet actuation system of FIGS. 10-12.

FIG. 17 shows a pitch chart that can be used with the invention.

Referring to FIGS. 1-17, after the delay in auto darkening lens W in the goggles 60, 420, 560, 590 has been set at the desired distance. The hitter 120 can take his/her place in the batter's box (next to home plate 80), behind the protective screen 70. In addition, an observer 95 can record the pitches on the pitch chart (FIG. 17). The observer 95 can position themselves in a location to both view the pitch and be able to hear the hitter's 120 verbal call of the pitch.

The observer 95 can record the both the actual pitch (based on their observations) and the called pitch from the hitter 120 on the Pitch Chart (FIG. 17). The Pitch Chart (FIG. 17) can be a series of 10 each 5×5 grids. The interior 3×3 grid represents the strikes zone, with the exterior cells representing balls out of the strike zone. The observer 95 can use the following symbols to record the pitches: F=Fastball, C=Curveball, SI=Slider and Ch=Change up. For each pitch, the observer 95 can record the hitter's 120 verbal call of pitch and location then record the actual pitch type and location on the same chart. The actual pitch can be circled. If both the hitter 120 and observer 95 are in agreement, a check mark will be placed next to the symbol on the grid. At the end of 10 pitches, the observer 95 can record the total number of correct pitch types called, the total number of locations called correctly and the distance from the pitcher that the auto darkening occurs.

The pitch chart in FIG. 17 can be used to tabulate and evaluate the training subject's 120 progress.

Referring to TABLE 1, the system setup motion sensor 150 with time delay can be adjusted based on speed of the pitched ball. A speed gun or other ball velocity detector can also be used to further train the hitter 120 to reach accuracy rates of identifying pitch types and pitch locations with the pitched balls being pitched at different speeds.

FIG. 18A is a side view of a configuration of the invention with a variable placement of the motion sensor 150 with cone 130. FIG. 18B is a top view of a configuration of the invention with a variable placement of the motion sensor 150 with cone 30 of FIG. 11A.

In the previous setup 1, the motion sensor assembly 20 with motion sensor 150 such as the BANNER Model# Q45VR3DL) was placed in the vicinity (within approximately 6') of the lead foot of the pitcher 100 as the triggering mechanism for the process to start the auto darkening of the lens W. The motion sensor assembly 20 was equipped with a timing chip such as the BANNER Model 45LM Series Modules that was adjusted manually by a turn screw.

FIGS. 18A-18B employs a different motion sensor 150, such as but not limited to a Banner Engineering, Model Q45VR3Dx with an approximate 10' Cone of Influence. By using this different sensor, the motion sensor can be placed on the ground, underneath the trajectory of the thrown ball, B, with its Cone of Influence directed vertically. As the ball B, passes thru the Cone of Influence, the motion sensor 150 is activated, sending a signal to the auto darkening lens W. in the goggles The benefits of FIGS. 18A, 18B includes several benefits. For example, there is no need for a timing chip, hence no need to adjust a timing chip for each hitter 120 or pitcher 100, and because the physical placement of the motion sensor, the hitter 120 knows exactly the distance in which the auto darkening lens W will activate.

While the invention has been described with a physical setup 1 that includes a separate pitcher 100, catcher 90, observer 95 and separate motion sensor arrangement 20, screen 70, goggle assembly 60, some or many of the components can be eliminated.

For example, devices, such as an automated device system can be used instead of or with the observer to identify the type of pitch and location of the pitched ball automatically for comparison with the hitter's 120 called out identification. Additionally, other components, such as but not limited to voice recognition used in smart phones and the like, can record the hitter calling out the pitch and location of the pitched balls, which can also be saved for later comparison with the accurate observations of the observer. Additionally, the observer can also be automated so that devices, such as but not limited to pitch speed and pitched ball location (in and out of the strike zone) can be recorded. See for example, U.S. Published Patent Application 2006/0030128 to Mosbey. Also, an automated pitcher device can collect actual data on pitch type, and the like. See for example, U.S. Pat. No. 6,983,741 to Donald. Other automated devices such as radar and speed guns can be used as the observer.

While the blackout lens have been described as being controlled by IR (infra red) light emitter and IR sensor, the lens can include other types of lens that change from transparent to opaque, such as but limited to be liquid crystals, and the like.

Although the disclosed embodiments show and describe goggles, such as welding goggles, the invention can be used with other types of eyewear, such as but not limited to spectacles, eyeglasses, or other types of adjustable lens such as contact lens, and the like.

Additionally, the protective screen can have lens, such as LCD (liquid crystal lens) with controls for causing the lens to be transparent to opaque and back, built thereon that blackout the pitcher to the hitter, so that the hitter does NOT need to wear goggles, and the like.

While the preferred embodiments show and describe wired components and some wireless components, the invention can be used with all wireless components and the like.

Additionally, a software simulation application of a pitcher pitching different types of pitches, at different speeds, that fall in and out of the strike zone, can be a downloadable App where the hitter can have a program on their smart phone, tablet, computer where the hitter is looking at a pitcher, and the screen is darkened at different increments. For example, the screen can be darkened where the pitched ball is 50 feet from the hitter (person looking at the computer screen). And the hitter again must successfully identify the type of pitch and location of the pitch at least 8 or 9 out of 10 times, before the screen is blacked out. Followed by the screen can be blacked out at another 10 foot increment (such as when the pitched ball is 40 feet from the pitcher, and so on, as described with the setup 1 in FIGS. 1-8. In addition to being used for training the software application can be game used for entertainment.

The accuracy training for playing sports and/or for playing computer games, can be based on pitch type (fastball, curve ball, slider and changeup) as well as location (in and out of the strike zone), and different pitched speeds. The lens and screen can be blacked out at selected distances for any one of these parameters, and for different combinations of these parameters. Tabulation and accuracy determination can also be for comparing the hitter's identifications with the observer's identifications with any one of these parameters, or any combination of these parameters.

Although the invention is describes as being applied to baseball and softball hitters, the invention can be used to train players where a ball is thrown, kicked or hit toward them, or where increased speed of situational recognition is beneficial or advantageous. Other sports, can include but are not limited to identify the trajectory of racquet balls, tennis balls, ping pong balls, as well as golf balls, soccer balls, and other sports, that use pucks, and the like, such as but not limited to hockey, and the like. Additionally, other sports, such as a football quarterback can have a lens in front of the them that blacks out at different times when the quarterback is seeing defensive coverage, and has to remember the coverage in order to set up their offensive play response.

Golfer Application

Figures 19A, 19B:
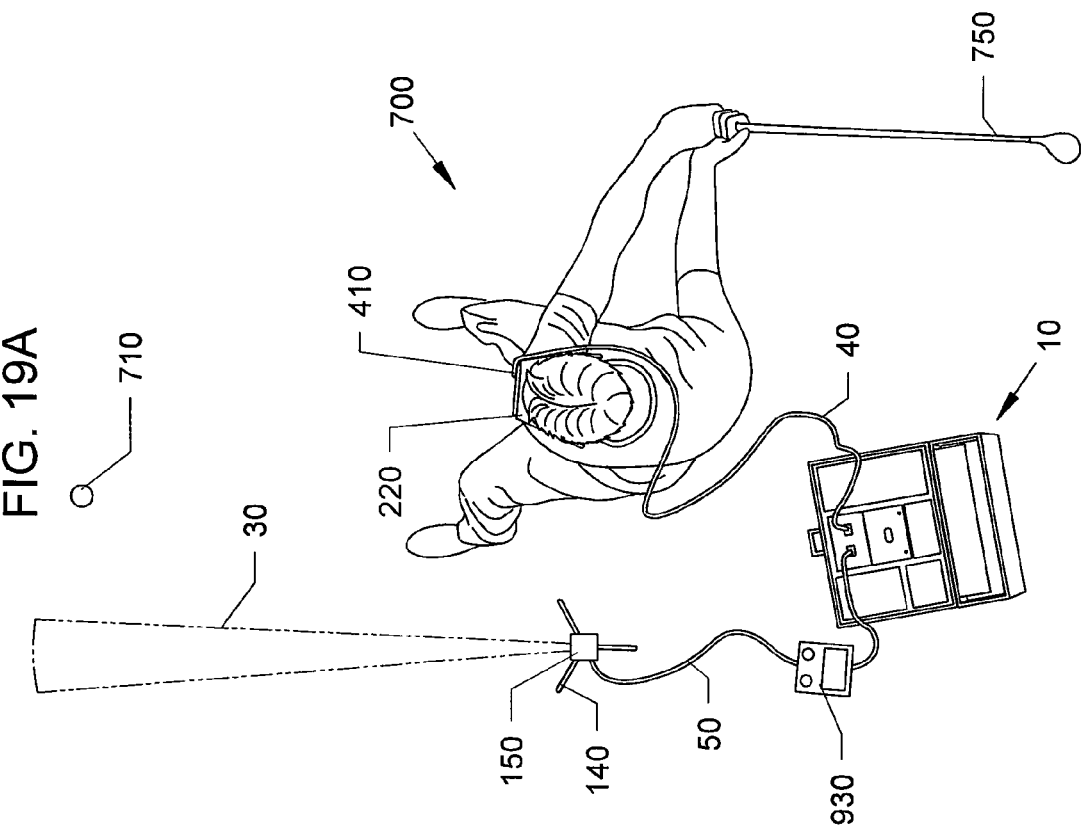
FIG. 19A is a top view of a golfer using the vision trainer, with the golfer is at the top of his back swing.
FIG. 19B is a front perspective view of the blackout goggles showing that the view screen is clear at the time of the back swing.

FIG. 19A is a top view of a golfer 700 using the vision trainer, with the golfer 700 is at the top of his back swing. The motion sensor 150 with sensor cone 30 on tripod 140 is set to sense the golf club 750 after it contacts the golf ball 710. This view shows the optional timer 930 attached by cable 50 to motion sensor 150, and to the portable vision training system carrying case 10. Timer 930 can be placed between the motion sensor 150 and the goggles 220 to delay the signal being sent from the sensor 150 to the goggles 220. This optional timer 930 can be used in any configuration of this system.

The system can limit vision of the golfer (player) from prior to striking the ball with the club to after the club strikes the ball. Any increment can be programmed into the delay from approximately ½ second before the ball is struck to approximately' second after the ball is struck, in approximately ⅒ second increments. The system can help train the golfer (player) to visually see up to the ball is struck, and condition the golfer (player) to cognitively remember spatial recognition of the placement of the ball, and try to rely on other senses to follow through with the golf swing. The system can help teach the golfer (player) to not have to look up during the golf swing to see where the ball is hit toward.

FIG. 19B is a front perspective view of the blackout goggles 220 of the blackout assembly 60 with IR light package 410, on the golfer 700 showing that the view screen (lens 720) is clear at the time of the back swing.

FIG. 20A is an updated view of FIG. 19A showing the path 760 of the golf club 750 and the path 740 of the golf ball just after the club has made contact 770 with the ball 710. The golf club 750 has passed through the motion sensor cone 30 and the view screen (lens dark 730) of the blackout goggles 220 which are blacked out. FIG. 20B is a front perspective view of the blackout goggles 220 of FIG. 19B showing that the view screen 730 is blacked out after the club 750 passes through the motion sensor cone 30.

Generally, golfers have a tendency to look up right after hitting a golf ball. The golf training system helps the golfer avoid looking up immediately upon hitting the golf ball since their field of vision is blacked out.

Tiltable Motion Sensor Base (Manual or Motor Controlled)

Figure 21A:
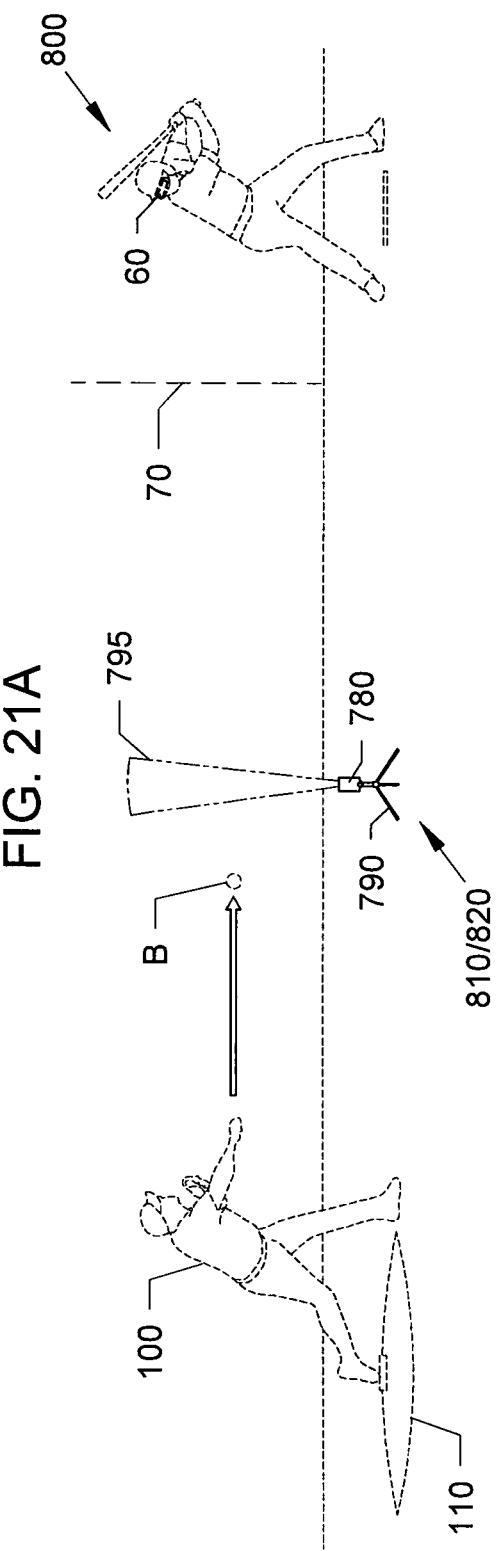
FIG. 21A is a side view of a system setup on a baseball infield similar to FIG. 18A, using a tilting sensor in a vertical upright position.
Figure 21B:
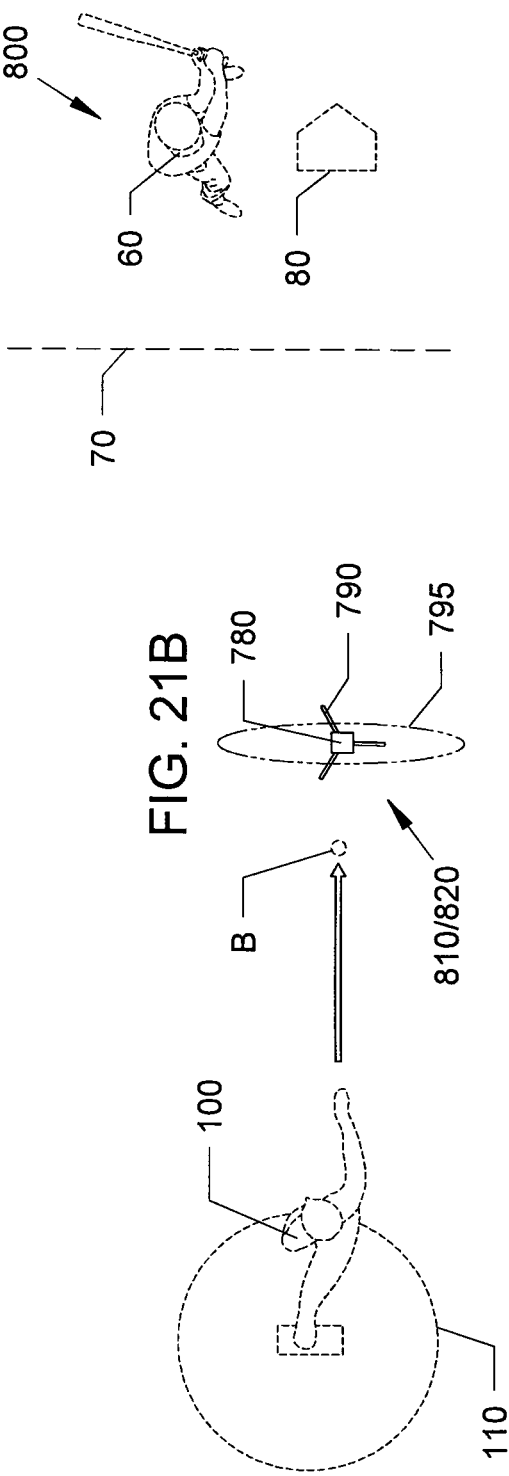
FIG. 21B is a top view of the system setup of FIG. 21A.

FIG. 21A is a side view of a system setup on a baseball playing field similar to FIG. 18A, using a tilting sensor 780 on a tripod 790 in a vertical upright position. Here, a pitcher 100 on a pitcher's mound 110 is pitching to a batter 800 at home plate 80. The upward looking sensor assembly looks for the ball B, to pass through the motion sensor cone 795. A signal is then sent that blacks out the goggles 60 being worn by the batter 800. FIG. 21B is a top view of the system setup of FIG. 21A.

Figure 21C:
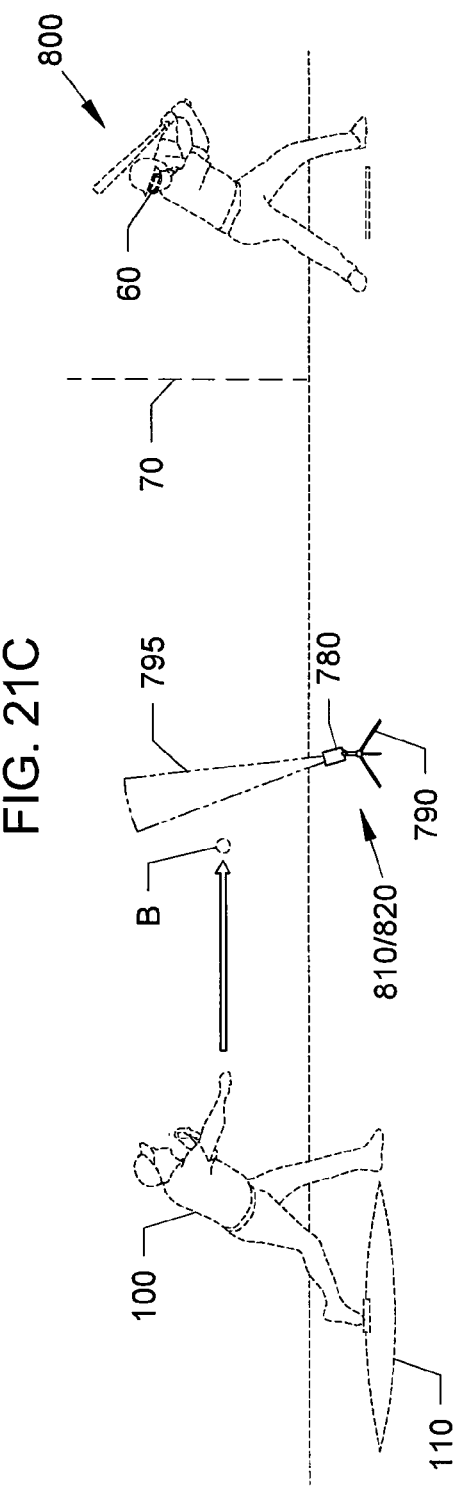
FIG. 21C is a side view of the system setup of FIG. 21A showing the upward looking sensor assembly tilted toward the pitcher such that the baseball will pass through the sensor cone sooner in the course of the pitch.

FIG. 21C is a side view of the system setup of FIG. 21A showing the upward looking sensor assembly 780 on tripod 790 tilted toward the pitcher 100 such that the baseball B will pass through the sensor cone 795 sooner in the course of the pitch. This will cause the sensor to send a signal to the blackout goggles 60 sooner in the course of the pitch.

Figure 21D:
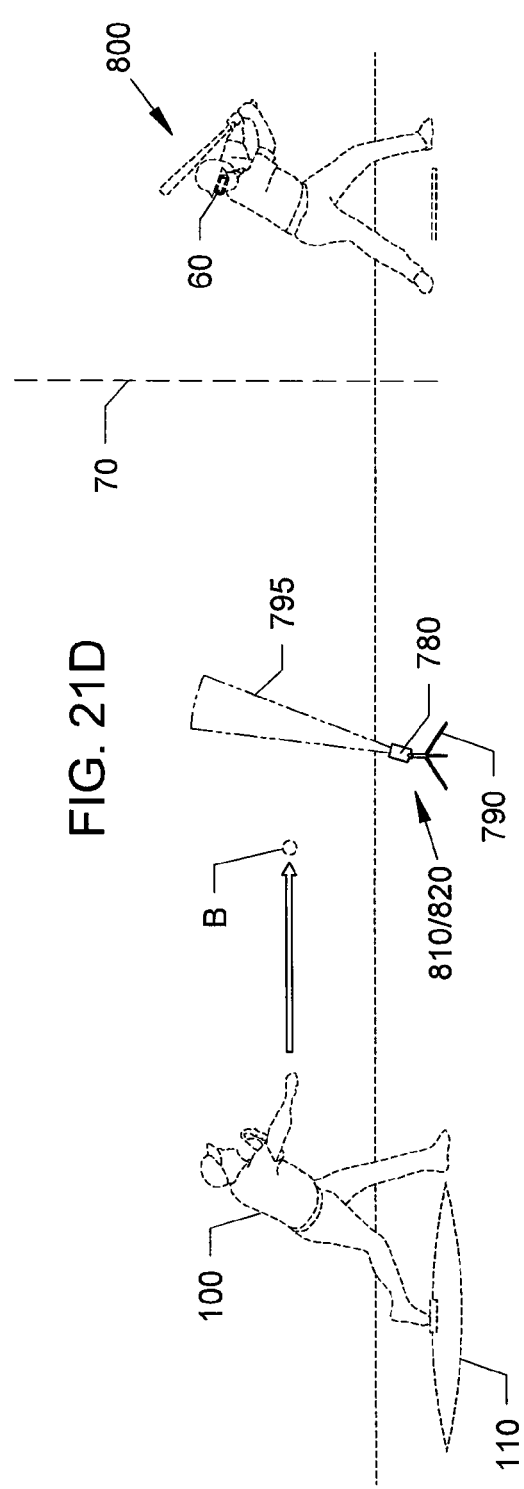
FIG. 21D is another side view of the system setup of FIG. 21A showing the upward looking sensor assembly tilted away from the pitcher such that the baseball will pass through the sensor cone later in the course of the pitch.

FIG. 21D is another side view of the system setup of FIG. 21A showing the upward looking sensor assembly 780 on tripod 790 tilted away from the pitcher 100 toward the batter 800 so that the baseball B will pass through the sensor cone later in the course of the pitch. This will cause the sensor 780 to send a signal to the blackout goggles 60 later in the course of the pitch.

FIG. 22 is an enlarged side view of a configuration of a manually adjustable 810 tilting, upward looking sensor assembly 780 on tripod 790, with a graduated tilt scale 860 on the side, which can be used with FIGS. 21A, 21B, 21C and 21D. Tilting the sensor 780 counter-clockwise in the direction of the pitcher 100 as shown by arrow 830 allows for the pitched ball B to through the sensor cone 30 sooner and sends the blackout signal earlier. Tilting the sensor 780 clockwise in the direction of the batter 800 sends the signal to the blackout goggle assembly 60 later.

FIG. 23 is an enlarged view of the tiltable sensor assembly 820 of FIG. 22 with the addition of a motor 910 to adjust the tilt and a remote control 880 connected by cable 920 with faster black out tilt button 890 and slower black out tilt button 900 control the motor. A cable 870 from the tilting sensor 850 can be connected to the system case 10 (shown in previous FIGS. 2-5).

The tiltable sensor assembly shown in FIGS. 21A-21D can be use with or without the protective shield which is described in the previous embodiments.

Within a sports environment, specifically baseball and/or softball, this system shown in FIGS. 21A-23 places an artificial limitation on the amount of time and/or distance the hitter can view the thrown object.

The tiltable system can be comprised of three main components: 1) a motion sensor 780/790 & 810/820 with an integrated adjustable timer relay chip, 2) a power source (in this case, a 12 volt rechargeable battery) and 3) a lens and goggle combination 60 wherein the lens can be activated to change from clear to opaque upon energizing an Infrared Emitter (ie an auto-darkening lens).

Motion Sensor—

The motion sensor 780/790 & 810/820 can come equipped with a 5-wire cable. Each of the 5 wires is a different color, signifying its purpose. Two of the wires are directed to the power source, 2 wires are directed to the Infrared Emitter and the 5$^{th}$ wire is not used.

Power Source—

The power source can be a commercially available 12 volt rechargeable battery

Lens/Goggle Combination—

The goggles 60 can be a commercially available welder's goggle with a 2"×4" opening for the lens. The lens has an auto darkening feature that, when the Infrared Emitter is energized above the Infrared Sensor of the goggles, causes the lens to become opaque for 2 seconds.

The integration of the above components is as follows:
4. The motion sensor is connected to the power supply and the Infrared Emitter thru cables (or wirelessly).
5. The Infrared Emitter is connected to motion sensor and the power supply thru cables (or wirelessly)
6. The power source is connected to both the motions sensor and infrared emitter, thereby closing the circuit.

How the System Functions

Environment—

The environment that this system is to be utilized in is a baseball or softball setting, specifically, the pitcher's mound to home plate whether on the actual playing field, bullpen or setting of similar nature.

System Set Up—

The system set up can be as follows:
6. Plug the cord of the motion sensor into the appropriate outlet
7. Plug the short cord of the Infrared Emitter into the plug of the long cord
8. Plug the long cord into the appropriate outlet
9. Attach the Infrared Emitter to the goggles making sure the Emitter is placed directly over the sensor on the lens
10. Energize the system.

System Placement—

The placement of the individual components can be as follows:

Motion Sensor—The motion sensor 780/790 & 810/820 can be placed in a location between the pitcher and the hitter. The zone of influence of the motion sensor is then arranged in a vertical manner as to have the pitched ball pass thru the beam array. The base of the motion sensor is equipped with a base capable of tilting either towards the pitcher or towards the hitter (either manually or automated). The tilt able base is equipped with a scale that correlates the angle tilted with distance added or decreased of the zone of influence in relation to the placement of the motion sensor. This capability will allow multiple hitters to train at multiple distances without having to re-adjust the position of the motion sensor.

Infrared Emitter/Goggles—The goggles 60 with the Infrared Emitter can be placed on the head of the batter 800. The batter would then stand next to home plate 80 in the same manner as he/she would to prepare to hit. Due to the defenseless nature of the hitter 800, it is imperative for safety concerns that the hitter be behind a protective screen.

Power Source—The power source can be placed anywhere as long as it does not interfere with the pitcher or hitter System Function—

When the pitched ball passes through the zone 795 of influence of the motion sensor, the motion sensor 780/790 & 810/820 will send a signal to energize the infrared emitter. The energized emitter will send an infrared light wave that is captured by the sensor on the lens. The internal components of the lens will then cause the lens to darken in $1/24{,}000$ of a second and remain dark for 2 seconds.

The delay by the timer relay chip can be adjusted from approximately 0.001 seconds to approximately 15 seconds. The range appropriate for use in this system should be from approximately 0.1 seconds to approximately 0.7 seconds, which is well within the functionality of this timer relay.

Purpose of System

First, the purpose of the system is based on the following 3 premises:
4. To be successful, the hitter 800 must know the type of pitch and the location of said pitch.
5. The trajectories of the 4 most common pitches (fastball, curveball, slider and changeup) are generally predictable.
6. By recognizing the pitch type and location earlier in the trajectory, the hitter 800 gains an advantage.

Therefore, based on these premises, the purpose of the system is to place artificial limitations on the amount of time and/or distance that the hitter can view the object. By doing so the hitter 800 is forced to process the details of each pitch with less information. Through repetition and feedback (discussed below), the hitter should be able to decrease the amount of time needed to determine a pitch type and location, thereby, giving the hitter more time to swing or not swing at the pitch.

Use of System

This system can be utilized in is a baseball or softball setting, specifically, the pitcher's mound to home plate whether on the actual playing field, bullpen or setting of similar nature. Four participants are required. They are as follows:
5. Pitcher
6. Catcher
7. Hitter
8. Observer charting pitches The pitcher, catcher and hitter can assume their natural positions with the exception that the hitter has a protective screen placed between him/her and the pitcher for safety precautions. The observer will position him/herself in a location where they can both verbally hear the hitter and visually see the entire trajectory of the thrown pitch.

The observer will have a chart with ten 5×5 grids signifying the 25 most probable locations of each pitch. The inner 3×3 grid represent the 9 zones of a strike (inside, middle, outside by upper, middle, lower). The remaining exterior zones represent balls thrown outside of the strike zone.

After the motion sensor has been placed at the desired location, the pitcher will begin throwing pitches to the catcher in a normal manner. For each pitch, the hitter will call out the pitch type, vertical and horizontal location of where the ball will cross home plate and whether ball is a strike or ball (ie. "fastball, low and away, ball", "curveball up and in, strike"). The observer will note the pitch type and location on the 5×5 grid called out by the hitter. The observer will then note on the same 5×5 grid the actual pitch type and location.

After a determine number of pitches, the hitter and observer will compare their results and a percentage will be tallied for the hitter for correctly calling both of the following:

Pitch type

Location of each pitch

Once the hitter can successfully and consistently call out the correct pitch type and location, the delay in the timer relay can be decreased. The procedure is then repeated until the hitter can, again, successfully and consistently call out the correct pitch type and location.

Benefits of Using System
4. This system can determine when a hitter is actually reading the details of the pitch. If the hitter using too much time to determine the pitch type and location, he/she has less time to determine whether to swing or not.
5. By using this system in a repetitious manner, it is possible for the hitter to process the information of each pitch quicker, thereby giving the hitter more time to determine whether to swing or not.
6. If the hitter is not making progress in processing the pitch information, it could signify an issue with the visual acuity of the hitter that had previously been undetected.

7. By using the motion sensor with a tilt able base, will allow multiple hitters to train at multiple distances without having to re-adjust the position of the motion sensor.

The tiltable sensor can be manually adjusted so that the cone can be moved toward the pitcher, straight up or toward the batter. As described the motion sensor can be manually adjusted to different tilt angles. The motor driven motion sensor can be adjusted remotely on-the-fly by an operator, that can change the cone tilt as selected with different pitches.

While a cone is described, other types of motion sensors can be used. For example a fan shaped cone can be used. Such a motion sensor can include but is not limited to a sensor generating a fan shape, such as the AG4 Series Safety Laser Scanner from Banner Engineering. Here, a two dimensional array of sensors can generate an approximately six foot radius to encompass up to approximately 12 degrees (forming a pie slice shape). The ball can be sensed as it passes through the tiltable pie shaped sensor shape.

The tiltable motion sensor allows for a single placement location of the motion sensor between the pitcher and the batter. The operator can select the tilt angle to adjust the amount of time the pitched ball is visible to the batter in real time during practice without having to physically move the motion sensor to different locations.

Secondary Training Applications

Within a sports environment, specifically baseball, softball or golf, this system places an artificial limitation on the amount of time and/or distance the hitter/golfer can view the object after contact with the bat and/or club.

The system can be comprised of three main components: 1) a motion sensor with an integrated adjustable timer relay chip, 2) a power source (in this case, a 12 volt rechargeable battery) and 3) a lens and goggle combination wherein the lens can be activated to change from clear to opaque upon energizing an Infrared Emitter (ie an auto-darkening lens).

Motion Sensor—

The motion sensor comes equipped with a 5-wire cable. Each of the 5 wires is a different color, signifying its purpose. Two of the wires are directed to the power source, 2 wires are directed to the Infrared Emitter and the $5^{th}$ wire is not used.

Additionally, the timer relay chip is used for its ability to delay the output signal from the motion sensor through a combination of on/off switches and a 15-turn screw.

Power Source—

The power source can be a commercially available 12 volt rechargeable battery

Lens/Goggle Combination—

The goggles 60 can be a commercially available welder's goggle with a 2"×4" opening for the lens. The lens has an auto darkening feature that, when the Infrared Emitter is energized above the Infrared Sensor of the goggles, causes the lens to become opaque for 2 seconds.

The integration of the above components is as follows:
7. The motion sensor is connected to the power supply and the Infrared Emitter thru cables (or wirelessly).
8. The Infrared Emitter is connected to motion sensor and the power supply thru cables (or wirelessly)
9. The power source is connected to both the motions sensor and infrared emitter, thereby closing the circuit.

Environment—

The environment that this system is to be utilized in is a baseball or softball setting, specifically, the pitcher's mound to home plate whether on the actual playing field, bullpen or setting of similar nature or a golf course driving range or setting of similar nature.

System Set Up—

The system set up is as follows:
11. Plug the cord of the motion sensor into the appropriate outlet
12. Plug the short cord of the Infrared Emitter into the plug of the long cord
13. Plug the long cord into the appropriate outlet
14. Attach the Infrared Emitter to the goggles making sure the Emitter is placed directly over the sensor on the lens
15. Energize the system.

System Placement—

The placement of the individual components are as follows:

Baseball/Softball Secondary Training Application

Motion Sensor—The motion sensor can be placed in a location where it can read the movement of either the pitcher's lead leg, pitcher's arm or ball leaving a pitching machine as it passes through the zone of influence of the beam. The motion sensor has a range of up to approximately 6 feet. However, signal strength is more consistent between approximately 2 feet to approximately 4 feet. The 2 primary factors in determining the placement of the motion sensor is 1) receiving a strong consistent signal from the motion sensor and 2) not interfering with the mechanics of the pitcher or safe operation of the pitching machine Infrared Emitter/Goggles—The goggles with the Infrared Emitter are placed on the head of the batter. The batter would then stand next to home plate in the same manner as he/she would to prepare to hit Power Source—The power source can be placed anywhere as long as it does not interfere with the pitcher, pitching machine or hitter.

System Function—

When the pitcher's lead leg, pitcher's arm or ball leaving the pitching machine crosses the zone of influence of the motion sensor, the motion sensor will send a signal to the timer relay chip. The timer relay chip will receive the signal and, per a predetermined delay, will then energize the infrared emitter for a predetermined amount of time. The energized emitter will send an infrared light wave that is captured by the sensor on the lens. The internal components of the lens will then cause the lens to darken in approximately 1/24,000 of a second and remain dark for 2 seconds.

The delay by the timer relay chip can be adjusted from approximately 0.001 seconds to approximately 15 seconds. The range appropriate for use in this system should be from approximately 0.1 seconds to approximately 0.7 seconds, which is well within the functionality of this timer relay.

Golf Training Application

Motion Sensor—The motion sensor is to be placed in a location where it can read the movement of the golf club after contact with the ball. The motion sensor has a range of up to 6 feet. However, signal strength is more consistent between approximately 2 feet to approximately 4 feet. The 2 primary factors in determining the placement of the motion sensor is 1) receiving a strong consistent signal from the motion sensor and 2) not interfering with the mechanics of the golfer Infrared Emitter/Goggles—The goggles with the Infrared Emitter are placed on the head of the golfer. The golfer would then stand next to ball in the same manner as he/she would to prepare to strike the ball.

Power Source—The power source can be placed anywhere as long as it does not interfere with the golfer System Function—

When golf club crosses the zone of influence of the motion sensor, the motion sensor will send a signal to the timer relay chip. The timer relay chip will receive the signal and, per a predetermined delay, will then energize the infrared emitter for a predetermined amount of time. The energized emitter will send an infrared light wave that is captured by the sensor on the lens. The internal components of the lens will then cause the lens to darken in 1/24,000 of a second and remain dark for 2 seconds.

The delay by the timer relay chip can be adjusted from 0.001 seconds to 15 seconds. The range appropriate for use in this system should be from 0.001 seconds to 0.1 seconds, which is well within the functionality of this timer relay.

Purpose of System

A common mechanical flaw of both baseball/softball hitters and golfers is to fail to see the ball making contact with the bat and/or club (aka "pull their head"). By restricting the vision of the hitter after contact, the incentive (and the ability) to see the result of the ball being struck is removed. Therefore the hitter will concentrate their training to visually see contact made with the ball.

Use of System

Baseball/Softball

This system is to be utilized in is a baseball or softball setting, specifically, the pitcher's mound to home plate whether on the actual playing field, bullpen, batting cage or setting of similar nature.

The timer relay chip in the motion sensor shall be adjusted so that the hitter can see the full path of the pitch and the auto darkening feature of the goggles occurs just as the ball passes the hitter. The hitter will assume their natural position in the batter's box and begin a normal hitting training session.

Golf

This system is to be utilized in is a golf course driving range or setting of similar nature.

The timer relay chip in the motion sensor shall be adjusted so that the auto darkening feature of the goggles occurs just the ball is struck. The golfer will assume their natural position next to the ball and begin a normal hitting training session.

Benefits of Using System

Baseball/Softball

By training with this system, the baseball/softball hitter will condition themselves to track the ball from the pitcher's hand (or pitching machine) to contact with the bat, thereby, seeing the entire pathway of the pitch.

Golf

By training with this system, the golfer will condition themselves to keep their eyes focused on the ball all the way through contact.

The term "approximately" can be +/−10% of the amount referenced. Additionally, preferred amounts and ranges can include the amounts and ranges referenced without the prefix of being approximately.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A vision training system for training golfers from looking up during a golf swing, comprising:
    a motion sensor triggered by a swinging golf club;
    a black out lens adapted to be in front of a golfer being trained; and
    a control changing the lens from transparent to opaque when the motion sensor is triggered by a swinging golf club travelling through a sensor path of the motion sensor.

2. The vision training system of claim 1, wherein the motion sensor includes:
    a support for supporting the motion sensor, the motion sensor generating an upwardly facing ray-type cone, wherein the motion sensor is triggered by the swinging of the golf club that travels through the ray-type cone.

3. The vision training system of claim 1, further comprising:
    an eyewear for supporting the blackout lens adapted to be worn by the golfer being trained.

4. The vision training system of claim 1, further comprising:
    a timer connected between the motion sensor and the black out lens for delaying the control for changing the lens from transparent to opaque.

5. A vision training system for training baseball and softball batters, to identify types of pitched balls and locations (strike or non-strike zone) of pitched balls in order to increase hitting accuracy, comprising:
    a tiltable motion sensor triggered when a pitched ball is sensed by the motion sensor;
    a black out lens adapted to be in front of a batter being trained; and
    a control for changing the lens from transparent to opaque at selected distances the pitched ball travels from the release of the pitched ball to before the pitched ball reaches the batter, wherein types of pitched balls and locations of pitched balls is identified.

6. The vision training system of claim 5, wherein the motion sensor includes:
    a support for the tiltable motion sensor for generating a fan shape of sensitivity, wherein the motion sensor is adapted to be triggered when the pitched ball is being released based on sensing motion of a leading foot of a pitcher.

7. The vision training system of claim 5, wherein the tiltable motion sensor is adapted to be tilted toward the pitcher.

8. The vision training system of claim 5, wherein the tiltable motion sensor is adapted to be tilted toward the batter.

9. The vision training system of claim 5, wherein the tiltable motion sensor includes:
    a graduated tilt scale for manually adjusting the tiltable motion sensor.

10. The vision training system of claim 5, wherein the tiltable motion sensor includes:
    a motor for tilting the tiltable motion sensor in selected tilt angles.

11. The vision training system of claim 10, wherein the tiltable motion sensor includes:
    a remote control for activating the motor for tilting the tiltable motion sensor in the selected tilt angles.

12. The vision training system of claim 5, further comprising:
    an eyewear for supporting the blackout lens adapted to be worn by the batter being trained; and a protective shield with the blackout lens, the protective shield adapted to be located in front of the batter, for substantially protecting the batter from being struck by the pitched ball.

13. The vision training system of claim 5, wherein the types of the pitched balls include:
fastballs, curveballs, sliders and changeups.

14. The vision training system of claim 13, wherein the locations of the pitched balls include:
the pitched balls being inside the strike zone or outside of the strike zone.

15. The system of claim 5, wherein the selected distances are between approximately zero and approximately 60 feet from the pitcher to the batter, or between approximately zero and approximately 45 feet from the pitcher to the batter.

16. The vision training system of claim 5, further comprising:
a chart for determining accuracy of the types of the pitched balls and the locations of the pitched balls identified from the batter in comparison with identifications of the types of pitched balls and the locations of the pitched balls identified from another source.

17. A vision training system for training batters to constantly follow the path of a pitched ball and prevent the batters from looking up from a batting swing, comprising:
a motion sensor triggered by a pitched ball;
a black out lens adapted to be in front of a pitcher being trained; and
a control changing the lens from transparent to opaque when the pitched ball travels through a sensor path of the motion sensor.

18. The vision training system of claim 17, wherein the motion sensor includes:
a support for the motion sensor for generating a cone of sensitivity, wherein the motion sensor is triggered when the pitched ball travels through a cone of sensitivity of the motion sensor.

19. The vision training system of claim 17, wherein the motion sensor includes:
a support for the motion sensor for generating a fan emission of sensitivity, wherein the motion sensor is triggered when the pitched ball travels through a fan emission of sensitivity of the motion sensor.

20. The vision training system of claim 17, further comprising:
eyewear for supporting the blackout lens adapted to be worn by the batter being trained; and
a protective shield adapted to be in front of the batter.

* * * * *